US010568930B2

(12) United States Patent
Van Der Weerden et al.

(10) Patent No.: US 10,568,930 B2
(45) Date of Patent: *Feb. 25, 2020

(54) AGENTS AND METHODS OF TREATMENT

(71) Applicant: Hexima Limited, Victoria (AU)

(72) Inventors: Nicole Van Der Weerden, Coburg (AU); Marilyn Anne Anderson, Keilor (AU); Jennifer Payne, Victoria (AU)

(73) Assignee: Hexima Limited, La Trobe University, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/306,307

(22) PCT Filed: Apr. 24, 2015

(86) PCT No.: PCT/AU2015/050195
§ 371 (c)(1),
(2) Date: Oct. 24, 2016

(87) PCT Pub. No.: WO2015/161348
PCT Pub. Date: Oct. 29, 2015

(65) Prior Publication Data
US 2017/0042966 A1  Feb. 16, 2017

(30) Foreign Application Priority Data
Apr. 24, 2014  (AU) .............................. 2014901480

(51) Int. Cl.
A61K 38/16 (2006.01)
A01N 37/46 (2006.01)
A61K 38/00 (2006.01)
A61K 9/00 (2006.01)
C07K 14/415 (2006.01)
A61K 31/343 (2006.01)
A61K 31/137 (2006.01)
A61K 31/4418 (2006.01)
A61K 31/7048 (2006.01)
A61K 31/201 (2006.01)
A61K 31/4196 (2006.01)
A61K 31/513 (2006.01)
A61K 31/496 (2006.01)
A01N 63/30 (2020.01)

(52) U.S. Cl.
CPC ............ A61K 38/168 (2013.01); A01N 37/46 (2013.01); A01N 63/30 (2020.01); A61K 9/0014 (2013.01); A61K 31/137 (2013.01); A61K 31/201 (2013.01); A61K 31/343 (2013.01); A61K 31/4196 (2013.01); A61K 31/4418 (2013.01); A61K 31/496 (2013.01); A61K 31/513 (2013.01); A61K 31/7048 (2013.01); A61K 38/005 (2013.01); C07K 14/415 (2013.01)

(58) Field of Classification Search
None
See application file for complete search history.

(56) References Cited

U.S. PATENT DOCUMENTS

| 9,713,632 B2 * | 7/2017 | Van Der Weerden ....................... A61K 38/168 |
| 9,943,564 B2 * | 4/2018 | Van Der Weerden ....................... A61K 38/168 |
| 2017/0049102 A1 * | 2/2017 | Van Der Weerden ....................... A01N 63/02 |

FOREIGN PATENT DOCUMENTS

| JP | 2003-507009 A | 2/2003 |
| JP | 2008-537675 A | 9/2008 |
| WO | WO 2001/009174 A2 | 2/2001 |
| WO | WO 2002/063011 A1 | 8/2002 |
| WO | WO 2003/000863 A2 | 1/2003 |
| WO | WO 2006/097110 A2 | 9/2006 |
| WO | WO 2008/018488 A1 | 2/2008 |
| WO | WO 2008/128289 A1 | 10/2008 |
| WO | WO 2009/094719 A1 | 8/2009 |
| WO | WO 2010/015024 A1 | 2/2010 |
| WO | WO 2012/027209 A2 | 3/2012 |
| WO | WO 2012/106759 A1 | 8/2012 |
| WO | WO 2014/078900 A1 | 5/2014 |

OTHER PUBLICATIONS

Hayes et al. "Identification and Mechanism of Action of the Plant Defensin NaD1 as a New Member of the Antifungal Drug Arsenal against Candida albicans," Antimicrobial Agents and Chemotherapy, 2013, vol. 57, No. 8, pp. 3667-3675 (Year: 2013).*

McCormack and Perry "Caspofungin a Review of its Use in the Treatment of Fungal Infections," Drugs 2005; 65 (14): 2049-2068 (Year: 2005).*

Revankar et al. "Melanized Fungi in Human Disease" Clinical Microbiology Reviews, Oct. 2010, p. 884-928 (Year: 2010).*

Carvalho, A. de O. and Gomes, V.M. 'Plant Defensins and Defensin-Like Peptides-Biological Activities and Biotechnological Applications', Current Pharmaceutical Design, 2011, vol. 17, pp. 4270-4293.

Van Der Weerden, N.L. and Anderson, M.A. 'Plant Defensins: Common Fold, Multiple Functions'. Fungal Biology Reviews, 2013, vol. 26, pp. 121-131.

Notice of Reasons for Rejection in Japanese Patent Application No. 2016-564054 dated Aug. 7, 2019.

* cited by examiner

Primary Examiner — Christina Bradley
(74) Attorney, Agent, or Firm — Knobbe, Martens, Olson & Bear, LLP

(57) ABSTRACT

Agents and formulations and cells including plant extracts are useful in a method for controlling pathogen infestation in human and animal subjects. A method for inhibiting growth or infestation of a pathogen in or on a human or animal subject, includes contacting the pathogen with an effective amount of a combination of a plant defensin or a functional natural or synthetic derivative or variant thereof and either: (i) a proteinase inhibitor; or (ii) a chemical pathogenicidic or pathogenostatic agent; in a combined amount effective to inhibit growth or infestation of the pathogen.

17 Claims, No Drawings
Specification includes a Sequence Listing.

SEQUENCE LISTING

```
<160> NUMBER OF SEQ ID NOS: 37

<210> SEQ ID NO 1
<211> LENGTH: 20
<212> TYPE: PRT
<213> ORGANISM: artificial
<220> FEATURE:
<223> OTHER INFORMATION: Amino acid sequence of C-terminal end amino
      acid sequence of NaD1 which ends and includes the most C-terminal
      invariant cysteine residue

<400> SEQUENCE: 1

Lys Phe Thr Asp Gly His Cys Ser Lys Ile Leu Arg Arg Cys Leu Cys
1               5                   10                  15

Thr Lys Pro Cys
            20

<210> SEQ ID NO 2
<211> LENGTH: 6
<212> TYPE: PRT
<213> ORGANISM: artificial
<220> FEATURE:
<223> OTHER INFORMATION: A modified amino acid sequence of a Class II
      Solanaceous defensin Loop1B region
<220> FEATURE:
<221> NAME/KEY: MISC_FEATURE
<222> LOCATION: (1)..(1)
<223> OTHER INFORMATION: X1 = A, R, N, D, C, Q, E, G, H, I, L, K, M, F,
      P, S, T, W, Y or V
<220> FEATURE:
<221> NAME/KEY: MISC_FEATURE
<222> LOCATION: (2)..(2)
<223> OTHER INFORMATION: X2 = A, R, N, D, C, Q, E, G, H, I, L, K, M, F,
      P, S, T, W, Y or V
<220> FEATURE:
<221> NAME/KEY: MISC_FEATURE
<222> LOCATION: (3)..(3)
<223> OTHER INFORMATION: X3 = A, R, N, D, C, Q, E, G, H, I, L, K, M, F,
      P, S, T, W, Y or V
<220> FEATURE:
<221> NAME/KEY: MISC_FEATURE
<222> LOCATION: (4)..(4)
<223> OTHER INFORMATION: X4 = A, R, N, D, C, Q, E, G, H, I, L, K, M, F,
      P, S, T, W, Y or V
<220> FEATURE:
<221> NAME/KEY: MISC_FEATURE
<222> LOCATION: (5)..(5)
<223> OTHER INFORMATION: X5 = A, R, N, D, C, Q, E, G, H, I, L, K, M, F,
      P, S, T, W, Y or V
<220> FEATURE:
<221> NAME/KEY: MISC_FEATURE
```

```
<222> LOCATION: (6)..(6)
<223> OTHER INFORMATION: X6 = A, R, N, D, C, Q, E, G, H, I, L, K, M, F,
      P, S, T, W, Y or V

<400> SEQUENCE: 2

Xaa Xaa Xaa Xaa Xaa Xaa
1               5

<210> SEQ ID NO 3
<211> LENGTH: 6
<212> TYPE: PRT
<213> ORGANISM: artificial
<220> FEATURE:
<223> OTHER INFORMATION: A modified amino acid sequence of a Class II
      Solanaceous defensin of Loop1B region
<220> FEATURE:
<221> NAME/KEY: MISC_FEATURE
<222> LOCATION: (1)..(1)
<223> OTHER INFORMATION: X1 = N, g, D, H, K, A, E, Q, T, P, L, M, S or R
<220> FEATURE:
<221> NAME/KEY: MISC_FEATURE
<222> LOCATION: (2)..(2)
<223> OTHER INFORMATION: X2 = K, R, G, H, L, N, F, I, S, T or Y
<220> FEATURE:
<221> NAME/KEY: MISC_FEATURE
<222> LOCATION: (3)..(3)
<223> OTHER INFORMATION: X3 = W, Y, H, L, G, F or P
<220> FEATURE:
<221> NAME/KEY: MISC_FEATURE
<222> LOCATION: (4)..(4)
<223> OTHER INFORMATION: X4 = P, K, S, R, H, T, E, V, N, Q, D or G
<220> FEATURE:
<221> NAME/KEY: MISC_FEATURE
<222> LOCATION: (5)..(5)
<223> OTHER INFORMATION: X5 = S, K, Y, F, G or H
<220> FEATURE:
<221> NAME/KEY: MISC_FEATURE
<222> LOCATION: (6)..(6)
<223> OTHER INFORMATION: X6 = P, V, L, T, A, F, N, K, R, M, G, H, I or Y

<400> SEQUENCE: 3

Xaa Xaa Xaa Xaa Xaa Xaa
1               5

<210> SEQ ID NO 4
<211> LENGTH: 6
<212> TYPE: PRT
<213> ORGANISM: artificial
<220> FEATURE:
<223> OTHER INFORMATION: A modified amino acid sequence of a Class II
      Solanaceous defensin of Loop1B region
<220> FEATURE:
<221> NAME/KEY: MISC_FEATURE
<222> LOCATION: (1)..(1)
<223> OTHER INFORMATION: X1 = N, H, Q, D, K or E
<220> FEATURE:
<221> NAME/KEY: MISC_FEATURE
<222> LOCATION: (2)..(2)
<223> OTHER INFORMATION: X2 = R, H, T, K or G
<220> FEATURE:
<221> NAME/KEY: MISC_FEATURE
<222> LOCATION: (3)..(3)
<223> OTHER INFORMATION: X3 = F, H, Y or W
<220> FEATURE:
<221> NAME/KEY: MISC_FEATURE
<222> LOCATION: (4)..(4)
<223> OTHER INFORMATION: X4 = P, K, S or R
<220> FEATURE:
<221> NAME/KEY: MISC_FEATURE
<222> LOCATION: (5)..(5)
<223> OTHER INFORMATION: X5 = G or F
<220> FEATURE:
<221> NAME/KEY: MISC_FEATURE
<222> LOCATION: (6)..(6)
<223> OTHER INFORMATION: X6 = P, V, I or N

```
<400> SEQUENCE: 4

Xaa Xaa Xaa Xaa Xaa Xaa
1               5

<210> SEQ ID NO 5
<211> LENGTH: 6
<212> TYPE: PRT
<213> ORGANISM: artificial
<220> FEATURE:
<223> OTHER INFORMATION: A modified amino acid sequence of a Class II
      Solanaceous defensin of Loop1B region
<220> FEATURE:
<221> NAME/KEY: MISC_FEATURE
<222> LOCATION: (1)..(1)
<223> OTHER INFORMATION: X1 = L, F, S, I, A, H, Y, Q, D, K or G
<220> FEATURE:
<221> NAME/KEY: MISC_FEATURE
<222> LOCATION: (2)..(2)
<223> OTHER INFORMATION: X2 = S, V, F, I, K, L, A, P, N, T, R, H or G
<220> FEATURE:
<221> NAME/KEY: MISC_FEATURE
<222> LOCATION: (3)..(3)
<223> OTHER INFORMATION: X3 = A, F, W, N, I, S, Y, P, L or H
<220> FEATURE:
<221> NAME/KEY: MISC_FEATURE
<222> LOCATION: (4)..(4)
<223> OTHER INFORMATION: X4 = K, G, E, R, A, P, F, Q, V or S
<220> FEATURE:
<221> NAME/KEY: MISC_FEATURE
<222> LOCATION: (5)..(5)
<223> OTHER INFORMATION: X5 = M, G, K, D, S, Y, P, E, N or F
<220> FEATURE:
<221> NAME/KEY: MISC_FEATURE
<222> LOCATION: (6)..(6)
<223> OTHER INFORMATION: X6 = V, T, M, S, W, A, P, G, E, K, L, H, I or N

<400> SEQUENCE: 5

```
Xaa Xaa Xaa Xaa Xaa Xaa
1               5
```

<210> SEQ ID NO 7
<211> LENGTH: 6
<212> TYPE: PRT
<213> ORGANISM: artificial
<220> FEATURE:
<223> OTHER INFORMATION: Amino acid sequence of Loop1B from NaD1

<400> SEQUENCE: 7

```
Asn Thr Phe Pro Gly Ile
1               5
```

<210> SEQ ID NO 8
<211> LENGTH: 47
<212> TYPE: PRT
<213> ORGANISM: artificial
<220> FEATURE:
<223> OTHER INFORMATION: HXP4 protein

<400> SEQUENCE: 8

```
Arg Glu Cys Lys Thr Glu Ser His Arg Phe Lys Gly Pro Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45
```

<210> SEQ ID NO 9
<211> LENGTH: 80
<212> TYPE: PRT
<213> ORGANISM: artificial
<220> FEATURE:
<223> OTHER INFORMATION: HXL001 Zea mays

<400> SEQUENCE: 9

```
Met Ala Leu Ser Arg Arg Met Ala Ala Pro Val Leu Val Leu Met Leu
1               5                   10                  15

Leu Leu Val Ala Thr Glu Leu Gly Thr Thr Lys Val Ala Glu Ala Arg
            20                  25                  30

His Cys Leu Ser Gln Ser His Arg Phe Lys Gly Leu Cys Met Ser Ser
        35                  40                  45

Asn Asn Cys Ala Asn Val Cys Gln Thr Glu Asn Phe Pro Gly Gly Glu
    50                  55                  60

Cys Lys Ala Glu Gly Ala Thr Arg Lys Cys Phe Cys Lys Lys Ile Cys
65                  70                  75                  80
```

<210> SEQ ID NO 10
<211> LENGTH: 82
<212> TYPE: PRT
<213> ORGANISM: artificial
<220> FEATURE:
<223> OTHER INFORMATION: HXL002 Triticum aestivum

<400> SEQUENCE: 10

```
Met Ala Leu Ser Arg Arg Met Ala Ala Ser Ala Leu Leu Leu Leu Val
1               5                   10                  15

Leu Leu Val Ala Thr Glu Met Gly Ala Thr Thr Val Lys Leu Ala Glu
            20                  25                  30

Ala Arg Asp Cys Leu Ser Gln Ser His Lys Phe Lys Gly Ala Cys Leu
        35                  40                  45
```

```
Ser Ser Ser Asn Cys Ala Ala Val Cys Arg Thr Glu Asn Phe Pro Asp
    50                  55                  60

Gly Glu Cys His Thr His Asn Phe Ala Arg Lys Cys Phe Cys Lys Arg
65                  70                  75                  80

Ala Cys

<210> SEQ ID NO 11
<211> LENGTH: 77
<212> TYPE: PRT
<213> ORGANISM: artificial
<220> FEATURE:
<223> OTHER INFORMATION: HXL004 Nicotiana benthamiana

<400> SEQUENCE: 11

Met Ala Gly Phe Pro Lys Val Leu Ala Thr Val Phe Leu Thr Leu Met
1               5                   10                  15

Leu Val Phe Ala Thr Glu Met Gly Pro Met Val Thr Glu Ala Arg Thr
                20                  25                  30

Cys Glu Ser Gln Ser His Arg Phe Lys Gly Leu Cys Phe Ser Arg Ser
            35                  40                  45

Asn Cys Ala Ser Val Cys His Thr Glu Gly Phe Asn Gly Gly His Cys
    50                  55                  60

Arg Gly Phe Arg Arg Arg Cys Phe Cys Thr Arg His Cys
65                  70                  75

<210> SEQ ID NO 12
<211> LENGTH: 75
<212> TYPE: PRT
<213> ORGANISM: artificial
<220> FEATURE:
<223> OTHER INFORMATION: HXL007 Cyamopsis tetragonoloba

<400> SEQUENCE: 12

Met Glu Lys Lys Ser Leu Ala Gly Phe Cys Cys Leu Phe Leu Ile Leu
1               5                   10                  15

Phe Leu Ala Gln Glu Ile Val Val Lys Thr Glu Ala Arg Thr Cys Glu
                20                  25                  30

Ser Leu Ala Asp Thr Tyr Arg Gly Pro Cys Phe Thr Asp Gly Ser Cys
            35                  40                  45

Asp Asp His Cys Lys Asn Lys Glu His Leu Ile Ser Gly Arg Cys Arg
    50                  55                  60

Asn Asp Phe Arg Cys Trp Cys Thr Arg Asn Cys
65                  70                  75

<210> SEQ ID NO 13
<211> LENGTH: 77
<212> TYPE: PRT
<213> ORGANISM: artificial
<220> FEATURE:
<223> OTHER INFORMATION: HXL008 picramnia pentandra

<400> SEQUENCE: 13

Met Asp Lys Lys Leu Phe Gly Phe Leu Leu Leu Met Phe Ile Leu Phe
1               5                   10                  15

Ala Ser Gln Glu Ser Met Val Gly Val Glu Ala Lys Val Cys Thr Lys
                20                  25                  30

Pro Ser Lys Phe Phe Lys Gly Leu Cys Gly Thr Asp Gly Ala Cys Thr
            35                  40                  45

Thr Ala Cys Arg Lys Glu Gly Leu His Ser Gly Tyr Cys Gln Leu Lys
    50                  55                  60
```

Gly Phe Leu Asn Ser Val Cys Val Cys Arg Lys His Cys
65                  70                  75

<210> SEQ ID NO 14
<211> LENGTH: 74
<212> TYPE: PRT
<213> ORGANISM: artificial
<220> FEATURE:
<223> OTHER INFORMATION: HXL013 Glycine max

<400> SEQUENCE: 14

Met Glu Arg Lys Thr Phe Gly Phe Leu Phe Leu Leu Leu Val Leu
1               5                   10                  15

Ala Ser Asp Val Thr Val Lys Arg Ala Glu Ala Lys Asp Cys Leu Thr
                20                  25                  30

Arg Arg His Gly Phe Gln Gly Arg Cys Leu Phe Asp Arg Gln Cys Ala
            35                  40                  45

His Val Cys Arg Ser Asp Gly Phe Ile Gly Gly Gln Cys Arg Gly Pro
        50                  55                  60

Leu Arg Lys Cys Phe Cys Ser Arg Pro Cys
65                  70

<210> SEQ ID NO 15
<211> LENGTH: 47
<212> TYPE: PRT
<213> ORGANISM: artificial
<220> FEATURE:
<223> OTHER INFORMATION: HXP34

<400> SEQUENCE: 15

Arg Glu Cys Lys Thr Glu Ser Gln His His Ser Phe Pro Cys Ile Thr
1               5                   10                  15

Lys Pro Pro Cys Arg Lys Ala Cys Ile Ser Glu Lys Phe Thr Asp Gly
                20                  25                  30

His Cys Ser Lys Ile Leu Arg Arg Cys Leu Cys Thr Lys Pro Cys
            35                  40                  45

<210> SEQ ID NO 16
<211> LENGTH: 47
<212> TYPE: PRT
<213> ORGANISM: artificial
<220> FEATURE:
<223> OTHER INFORMATION: HXP35

<400> SEQUENCE: 16

Arg Glu Cys Lys Thr Glu Ser Asp Thr Tyr Arg Gly Val Cys Ile Thr
1               5                   10                  15

Lys Pro Pro Cys Arg Lys Ala Cys Ile Ser Glu Lys Phe Thr Asp Gly
                20                  25                  30

His Cys Ser Lys Ile Leu Arg Arg Cys Leu Cys Thr Lys Pro Cys
            35                  40                  45

<210> SEQ ID NO 17
<211> LENGTH: 46
<212> TYPE: PRT
<213> ORGANISM: artificial
<220> FEATURE:
<223> OTHER INFORMATION: HXP37

<400> SEQUENCE: 17

Arg Glu Cys Lys Thr Glu Ser Glu Gly Trp Gly Lys Cys Ile Thr Lys
1               5                   10                  15

```
Pro Pro Cys Arg Lys Ala Cys Ile Ser Glu Lys Phe Thr Asp Gly His
            20                  25                  30

Cys Ser Lys Ile Leu Arg Arg Cys Leu Cys Thr Lys Pro Cys
        35                  40                  45

<210> SEQ ID NO 18
<211> LENGTH: 47
<212> TYPE: PRT
<213> ORGANISM: artificial
<220> FEATURE:
<223> OTHER INFORMATION: HXP58

<400> SEQUENCE: 18

Arg Glu Cys Lys Thr Glu Ser Lys Thr Trp Ser Gly Asn Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 19
<211> LENGTH: 49
<212> TYPE: PRT
<213> ORGANISM: artificial
<220> FEATURE:
<223> OTHER INFORMATION: HXP72

<400> SEQUENCE: 19

Gly Thr Cys Lys Ala Glu Cys His Arg Phe Lys Gly Pro Cys Ile Asn
1               5                   10                  15

Lys Ala Pro Cys Val Lys Cys Cys Lys Ala Gln Pro Glu Lys Phe Thr
            20                  25                  30

Asp Gly His Cys Ser Lys Ile Leu Arg Arg Cys Leu Cys Thr Lys Pro
        35                  40                  45

Cys

<210> SEQ ID NO 20
<211> LENGTH: 47
<212> TYPE: PRT
<213> ORGANISM: artificial
<220> FEATURE:
<223> OTHER INFORMATION: HXP91

<400> SEQUENCE: 20

Arg Glu Cys Lys Thr Glu Ser Asp Lys Tyr Arg Gly Pro Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 21
<211> LENGTH: 47
<212> TYPE: PRT
<213> ORGANISM: artificial
<220> FEATURE:
<223> OTHER INFORMATION: HXP92

<400> SEQUENCE: 21

Arg Glu Cys Lys Thr Glu Ser Lys Thr Phe Lys Gly Ile Cys Ile Thr
1               5                   10                  15
```

-continued

```
Lys Pro Pro Cys Arg Lys Ala Cys Ile Ser Glu Lys Phe Thr Asp Gly
             20                  25                  30

His Cys Ser Lys Ile Leu Arg Arg Cys Leu Cys Thr Lys Pro Cys
         35                  40                  45

<210> SEQ ID NO 22
<211> LENGTH: 47
<212> TYPE: PRT
<213> ORGANISM: artificial
<220> FEATURE:
<223> OTHER INFORMATION: HXP95

<400> SEQUENCE: 22

Lys Asp Cys Lys Arg Glu Ser His Arg Phe Lys Gly Pro Cys Ile Thr
1               5                   10                  15

Lys Leu Pro Cys Arg Arg Ala Cys Ile Ser Glu Lys Phe Ala Asp Gly
             20                  25                  30

His Cys Ser Lys Ile Leu Arg Arg Cys Leu Cys Thr Lys Pro Cys
         35                  40                  45

<210> SEQ ID NO 23
<211> LENGTH: 48
<212> TYPE: PRT
<213> ORGANISM: artificial
<220> FEATURE:
<223> OTHER INFORMATION: HXP107

<400> SEQUENCE: 23

Gln Gln Ile Cys Lys Ala Pro Ser His Arg Phe Lys Gly Pro Cys Phe
1               5                   10                  15

Met Asp Ser Ser Cys Arg Lys Tyr Cys Ile Lys Glu Lys Phe Thr Gly
             20                  25                  30

Gly His Cys Ser Lys Leu Gln Arg Lys Cys Leu Cys Thr Lys Pro Cys
         35                  40                  45

<210> SEQ ID NO 24
<211> LENGTH: 80
<212> TYPE: PRT
<213> ORGANISM: artificial
<220> FEATURE:
<223> OTHER INFORMATION: HXL015

<400> SEQUENCE: 24

Met Ala Pro Ser Arg Arg Met Val Ala Ser Ala Phe Leu Leu Leu Ala
1               5                   10                  15

Ile Leu Val Ala Thr Glu Met Gly Thr Thr Lys Val Ala Glu Ala Arg
             20                  25                  30

His Cys Leu Ser Gln Ser His Arg Phe Lys Gly Met Cys Val Ser Ser
         35                  40                  45

Asn Asn Cys Ala Asn Val Cys Arg Thr Glu Ser Phe Pro Asp Gly Glu
     50                  55                  60

Cys Lys Ser His Gly Leu Glu Arg Lys Cys Phe Cys Lys Lys Val Cys
65                  70                  75                  80

<210> SEQ ID NO 25
<211> LENGTH: 48
<212> TYPE: PRT
<213> ORGANISM: artificial
<220> FEATURE:
<223> OTHER INFORMATION: HXL012 Amaranthus retroflexus

<400> SEQUENCE: 25
```

```
Arg Met Cys Lys Ala Pro Ser Lys Leu Phe Arg Gly Met Cys Gly Ile
1               5                   10                  15

Arg Asp Ser Asn Cys Asp Ser Val Cys Arg Ala Glu Gly Met Ala Ala
                20                  25                  30

Gly Asp Cys His Gly Leu Arg Arg Cys Ile Cys Ser Arg Pro Cys
            35                  40                  45

<210> SEQ ID NO 26
<211> LENGTH: 49
<212> TYPE: PRT
<213> ORGANISM: artificial
<220> FEATURE:
<223> OTHER INFORMATION: HXL001 Zea mays

<400> SEQUENCE: 26

Arg His Cys Leu Ser Gln Ser His Arg Phe Lys Gly Leu Cys Met Ser
1               5                   10                  15

Ser Asn Asn Cys Ala Asn Val Cys Gln Thr Glu Asn Phe Pro Gly Gly
                20                  25                  30

Glu Cys Lys Ala Glu Gly Ala Thr Arg Lys Cys Phe Cys Lys Lys Ile
            35                  40                  45

Cys

<210> SEQ ID NO 27
<211> LENGTH: 49
<212> TYPE: PRT
<213> ORGANISM: artificial
<220> FEATURE:
<223> OTHER INFORMATION: HXL002 Triticum aestivum

<400> SEQUENCE: 27

Arg Asp Cys Leu Ser Gln Ser His Lys Phe Lys Gly Ala Cys Leu Ser
1               5                   10                  15

Ser Ser Asn Cys Ala Ala Val Cys Arg Thr Glu Asn Phe Pro Asp Gly
                20                  25                  30

Glu Cys His Thr His Asn Phe Ala Arg Lys Cys Phe Cys Lys Arg Ala
            35                  40                  45

Cys

<210> SEQ ID NO 28
<211> LENGTH: 47
<212> TYPE: PRT
<213> ORGANISM: artificial
<220> FEATURE:
<223> OTHER INFORMATION: HXL004 Nicotiana benthamiana

<400> SEQUENCE: 28

Arg Thr Cys Glu Ser Gln Ser His Arg Phe Lys Gly Leu Cys Phe Ser
1               5                   10                  15

Arg Ser Asn Cys Ala Ser Val Cys His Thr Glu Gly Phe Asn Gly Gly
                20                  25                  30

His Cys Arg Gly Phe Arg Arg Cys Phe Cys Thr Arg His Cys
            35                  40                  45

<210> SEQ ID NO 29
<211> LENGTH: 47
<212> TYPE: PRT
<213> ORGANISM: artificial
<220> FEATURE:
<223> OTHER INFORMATION: HXL007 Cyamopsis tetragonoloba

<400> SEQUENCE: 29
```

```
Arg Thr Cys Glu Ser Leu Ala Asp Thr Tyr Arg Gly Pro Cys Phe Thr
1               5                   10                  15

Asp Gly Ser Cys Asp His Cys Lys Asn Lys Glu His Leu Ile Ser
            20                  25                  30

Gly Arg Cys Arg Asn Asp Phe Arg Cys Trp Cys Thr Arg Asn Cys
            35                  40                  45
```

<210> SEQ ID NO 30
<211> LENGTH: 50
<212> TYPE: PRT
<213> ORGANISM: artificial
<220> FEATURE:
<223> OTHER INFORMATION: HXL008 Picramnia pentandra

<400> SEQUENCE: 30

```
Lys Val Cys Thr Lys Pro Ser Lys Phe Phe Lys Gly Leu Cys Gly Thr
1               5                   10                  15

Asp Gly Ala Cys Thr Thr Ala Cys Arg Lys Glu Gly Leu His Ser Gly
            20                  25                  30

Tyr Cys Gln Leu Lys Gly Phe Leu Asn Ser Val Cys Val Cys Arg Lys
            35                  40                  45

His Cys
    50
```

<210> SEQ ID NO 31
<211> LENGTH: 47
<212> TYPE: PRT
<213> ORGANISM: artificial
<220> FEATURE:
<223> OTHER INFORMATION: HXL013 glycine max

<400> SEQUENCE: 31

```
Lys Asp Cys Leu Thr Arg Arg His Gly Phe Gln Gly Arg Cys Leu Phe
1               5                   10                  15

Asp Arg Gln Cys Ala His Val Cys Arg Ser Asp Gly Phe Ile Gly Gly
            20                  25                  30

Gln Cys Arg Gly Pro Leu Arg Lys Cys Phe Cys Ser Arg Pro Cys
            35                  40                  45
```

<210> SEQ ID NO 32
<211> LENGTH: 49
<212> TYPE: PRT
<213> ORGANISM: artificial
<220> FEATURE:
<223> OTHER INFORMATION: HXL015 Oryza sativa

<400> SEQUENCE: 32

```
Arg His Cys Leu Ser Gln Ser His Arg Phe Lys Gly Met Cys Val Ser
1               5                   10                  15

Ser Asn Asn Cys Ala Asn Val Cys Arg Thr Glu Ser Phe Pro Asp Gly
            20                  25                  30

Glu Cys Lys Ser His Gly Leu Glu Arg Lys Cys Phe Cys Lys Lys Val
            35                  40                  45

Cys
```

<210> SEQ ID NO 33
<211> LENGTH: 51
<212> TYPE: PRT
<213> ORGANISM: artificial
<220> FEATURE:
<223> OTHER INFORMATION: HXL009

```
<400> SEQUENCE: 33

Thr Val Cys Met Arg His Asn Asn Phe Tyr His Gly Pro Cys Met Ser
1               5                   10                  15

Asn Lys Asp Cys Ala Asn Ser Cys Val Gln His Asn Leu Gly Val Gly
            20                  25                  30

Gly Tyr Cys Arg Gly Lys Ile Pro Phe Asn Lys Glu Cys Met Cys Thr
        35                  40                  45

Phe Glu Cys
    50

<210> SEQ ID NO 34
<211> LENGTH: 50
<212> TYPE: PRT
<213> ORGANISM: artificial
<220> FEATURE:
<223> OTHER INFORMATION: HXL035 Picramnia pentandra

<400> SEQUENCE: 34

Lys Val Cys Thr Lys Pro Ser Lys Phe Phe Lys Gly Leu Cys Gly Phe
1               5                   10                  15

Asp Arg Asp Cys Thr Val Ala Cys Lys Lys Glu Gly Leu Ala Ser Gly
            20                  25                  30

Phe Cys Gln Asn Lys Gly Phe Phe Asn Val Val Cys Val Cys Arg Lys
        35                  40                  45

Pro Cys
    50

<210> SEQ ID NO 35
<211> LENGTH: 50
<212> TYPE: PRT
<213> ORGANISM: artificial
<220> FEATURE:
<223> OTHER INFORMATION: HXL036 Picramnia pentandra

<400> SEQUENCE: 35

Lys Val Cys Thr Lys Pro Ser Lys Phe Phe Lys Gly Leu Cys Gly Ala
1               5                   10                  15

Asp Arg Asp Cys Thr Val Ala Cys Lys Lys Glu Gly Leu Ala Thr Gly
            20                  25                  30

Phe Cys Gln Lys Lys Gly Phe Phe Asn Phe Val Cys Val Cys Arg Lys
        35                  40                  45

Pro Cys
    50

<210> SEQ ID NO 36
<211> LENGTH: 49
<212> TYPE: PRT
<213> ORGANISM: artificial
<220> FEATURE:
<223> OTHER INFORMATION: Petunia hybrida (PhD1A)

<400> SEQUENCE: 36

Ala Thr Cys Lys Ala Glu Cys Pro Thr Trp Asp Gly Ile Cys Ile Asn
1               5                   10                  15

Lys Gly Pro Cys Val Lys Cys Cys Lys Ala Gln Pro Glu Lys Phe Thr
            20                  25                  30

Asp Gly His Cys Ser Lys Ile Leu Arg Arg Cys Leu Cys Thr Lys Pro
        35                  40                  45

Cys
```

-continued

```
<210> SEQ ID NO 37
<211> LENGTH: 47
<212> TYPE: PRT
<213> ORGANISM: artificial
<220> FEATURE:
<223> OTHER INFORMATION: Nicotiana occidentalis ssp Obliqua

<400> SEQUENCE: 37

Arg Gln Cys Lys Ala Glu Ser Asn Thr Phe Thr Gly Ile Cys Ile Ala
1               5                   10                  15

Lys Pro Pro Cys Arg Gln Ala Cys Ile Arg Glu Lys Phe Thr Asp Gly
                20                  25                  30

His Cys Ser Lys Val Leu Arg Arg Cys Leu Cys Thr Lys Arg Cys
            35                  40                  45
```

AGENTS AND METHODS OF TREATMENT

INCORPORATION BY REFERENCE TO ANY PRIORITY APPLICATIONS

This application is the U.S. National Phase of International Application No. PCT/AU2015/050195, filed Apr 24, 2015, designating the U.S. and claiming priority to Australian Patent Application No. 2014901480, filed Apr 24, 2014. Any and all applications for which a foreign or domestic priority claim is identified here or in the Application Data Sheet as filed with the present application are hereby incorporated by reference under 37 CFR 1.57.

FIELD OF THE INVENTION

The present disclosure relates generally to a method for controlling pathogen infestation in human and animal subjects and agents and formulations and cells including plant extracts useful for same.

BACKGROUND OF THE INVENTION

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Pathogen infestation can lead to significant health issues in humans and animals. These health issues contribute to ever escalating human and animal healthcare expenditure. Even preventative measures require significant fiscal outlays.

Agricultural losses due to animal including poultry pathogens such as fungal pathogens, for example, are a major problem in the agricultural industry and each year millions of dollars are spent on the topical application by fungicides to curb these losses.

Although chemical and antibiotic pathogenicides including fungicides have been successful in human and veterinary medicine, the increasing use of these agents is providing selective pressure for emergence of resistant strains of pathogens. There is clearly a need to develop alternative mechanisms of controlling infestation by human and animal pathogens or to more efficiently manage existing agents.

Plants have evolved various systems to provide some natural protection against pathogen infestation. These innate immune systems comprise both constitutive or pre-formed and inducible components. Hithertofore, there has not been significant recognition of the potential application of the components of plant innate immune systems to non-plant hosts. Examples of these components are small, disulfide-rich proteins which play a large role in both the constitutive and inducible aspects of plant immunity. They can be categorized into families based on their cysteine arrangements and include the thionins, snakins, thaumatin-like proteins, hevein- and knottin-type proteins, lipid transfer proteins, hairpinins and cyclotides as well as defensins.

Plant defensins are small (45-54 amino acids), basic proteins with four to five disulfide bonds (Janssen et al. (2003) *Biochemistry* 42(27):8214-8222). They share a common disulfide bonding pattern and a common structural fold, in which a triple-stranded, antiparallel β-sheet is tethered to an α-helix by three disulfide bonds, forming a cysteine-stabilized αβ motif. A fourth disulfide bond also joins the N- and C-termini leading to an extremely stable structure. A variety of functions has been attributed to defensins, including anti-bacterial activity, protein synthesis inhibition and α-amylase and protease inhibition (Colilla et al. (1990) *FEBS Lett* 270(1-2):191-194; Bloch and Richardson (1991) *FEBS Lett* 279(1):101-104).

The structure of defensins consists of seven 'loops', defined as the regions between cysteine residues. Loop 1 encompasses the first β-strand (1A) as well as most of the flexible region that connects this β-strand to the α-helix (1B) between the first two invariant cysteine residues. Loops 2, 3 and the beginning of 4 (4A) make up the α-helix, while the remaining loops (4B-7) make up β-strands 2 and 3 and the flexible region that connects them (β-hairpin region) (van der Weerden et al. (2013) *Cell Mol Life Sci* 70 (19): 3545-3570). This hairpin region of plant defensins forms a γ-core motif that is found in many anti-microbial peptides of diverse classes (Yount and Yeaman (2005) *Protein Pept Lett* 12(1):49-67).

Despite their conserved structure, plant defensins share very little sequence identity, with only the eight cysteine residues completely conserved. The cysteine residues are commonly referred to as "invariant cysteine residues", as their presence and location are conserved amongst defensins. Based on sequence similarity, plant defensins can be categorized into different groups. Within each group, sequence homology is relatively high whereas inter-group amino acid similarity is low (van der Weerden et al. (2013) *Cell Mol Life Sci* 70 (19): 3545-3570).

Plant defensins can be divided into two major classes. Class I defensins consist of an endoplasmic reticulum (ER) signal sequence followed by a mature defensin domain. Class II defensins are produced as larger precursors with C-terminal pro-domains or pro-peptides (CTPPs) of about 33 amino acids. Most of the Class II defensins identified to date have been found in *Solanaceous* plant species.

Class II *Solanaceous* defensins are expressed in floral tissues. They include NaD1, which is expressed in high concentrations in the flowers of ornamental tobacco *Nicotiana alata* (Lay et al. (2003) *Plant Physiol* 131(3):1283-1293). The anti-fungal activity of this peptide involves binding to the cell wall, permeabilization of the plasma membrane and entry of the peptide into the cytoplasm of the hyphae (van der Weerden et al. (2008) *J Biol Chem* 283 (21):14445-14452) and induction of reactive oxygen species (Hayes et al. (2014) *Cell Mol Life Sci*. February 2014, on line ISSN 1420-682X).

Class II *Solanaceous* defensins have variable degrees of activity against plant fungi. Some Class I defensins exhibit very low anti-fungal activity. Very little research has been conducted hithertofore on the effects of plant defensins on non-plant pathogens.

Defensins with highly divergent sequences act via different mechanism of actions. Permeabilization of the plasma membrane is a common feature that is observed for a number of defensins. However, the mechanism of permeabilization and its role in cell death differs between different defensins. Some defensins cause membrane permeabilization at high concentrations, but not at the concentration required for complete growth inhibition. In fact, the concentration of these proteins required to cause significant membrane permeabilization is around 20 times that required for growth inhibition. These proteins do cause slight membrane permeabilization at concentrations required for growth inhibition but only after long time periods (>150 mins). This is likely a result of fungal cell death that occurs after this time. The SYTOX green assay described in U.S.

patent application Ser. No. 12/535,443 has been successfully used to assay permeabilization.

In contrast, to some other plant defensins, the plant defensin NaD1 causes significant membrane permeabilization at concentrations corresponding to the IC50. Permeabilization by NaD1 begins within 15 minutes and reaches its maximum after 80 minutes (van der Weerden et al. (2010) *J Biol Chem* 285(48):37513-37520). NaD1 also causes some membrane permeabilization at low concentrations that do not cause growth inhibition (van der Weerden et al. (2008) *J Biol Chem* 283(20:14445-14452). Difference in the permeabilization kinetics between defensins is likely due to differences in the mechanism of action of the proteins. Hence, there is a role in using permeabilization assays to select appropriate defensins.

There is a need to develop protocols to more effectively manage pathogen infection and infestation in humans and animals. The ability to more efficiently facilitate control of pathogens with reduced application of antibiotic agents or without the need for this application altogether will reduce the potential for resistant strains of pathogens to emerge. This is of particular concern, not only in hospital and healthcare facilities, but also within high density animal facilities.

SUMMARY OF THE INVENTION

Nucleotide and amino acid sequences are referred to by a sequence identifier number (SEQ ID NO). The SEQ ID NOs correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present disclosure teaches a method for inhibiting growth or infestation of a pathogen in or on a human or animal subject, the method comprising contacting the pathogen with an effective amount of a combination of a plant defensin or a functional natural or synthetic derivative or variant thereof and either: (i) a proteinase inhibitor; or (ii) a chemical pathogenicidic or pathogenistatic agent; in a combined effective amount to inhibit growth or infestation of the pathogen. In an embodiment, the combination of the defensin and the (i) proteinase inhibitor; or (ii) chemical agent; has a synergistic effect compared to the use of each alone at the same individual dose as used in the combination.

In an embodiment, the plant defensin or its functional natural or synthetic derivative or variant is a permeabilizing defensin. These include Class I defensins and Class II Solanaceous defensins. Examples include NaD1 (Q8GTMO), TPP3 (AAA80496), PhD1 (Q8H6Q1), PhD1A (SEQ ID NO:36), PhD2 (Q8H6Q0), FST (p32026), NoD173 (SEQ ID NO:37), HXL001, HXL002, HXL004, HXL007, HXL008, HXL009, HXL012, HXL013, HXL015, HXL035 and HXL036. In an embodiment, the permeabilizing defensin is a functional natural or synthetic derivative or variant thereof Examples of synthetic variants include where a Loop1B from a Class I defensin replaces the Loop1B from the Solanaceous Class II defensin. These include HXP4, HXP34, HXP35, HXP37, HXP58, HXP72, HXP91, HXP92, HXP95 and HXP107.

Reference to a "proteinase inhibitor" includes a plant proteinase inhibitor or a proteinase inhibitor of non-plant origin as well as a precursor form which requires to be processed into an active form. Where a proteinase inhibitor is used in generating a formulation with a defensin, any precursor form is activated prior to use. Examples of proteinase inhibitors include serine and cysteine proteinase inhibitors such as NaCys1, NaCys2, NaCys3, NaCys4, HvCPI6, SlCys9, Oc-Ia, Oc-Ib, Oc-Ic, Oc-Id, StPin1A, At2g38870, CI-1B, CI-2, At2g43510 and BPTI.

Reference to a "chemical agent" includes a proteinaceous and non-proteinaceous chemical molecule. Chemical pathogenicidic or pathogenistatic agents include a fungicide selected from the list consisting of ciclopirox, terbinafine, fenpropimorph, ketoconazole, intraconazole, fluconazole, amorolfine, amphotericin, azole, polyene, echinocandin, allylamine, griseofulvin, tolnaftate, benzoxaborole, aganocide, flucytosine, haloprogin, polygodial and undecylenic acid. An example of an echinocandin fungicide is caspofungin. Chemical cell wall synthase inhibitors are also contemplated herein. Proteinaceous pathogenicidic or pathogenistatic agents include a β-glucan synthase inhibitor and a chitin synthase inhibitor as well as other cell wall synthase inhibitors.

It is surprisingly determined herein that the combination of a plant defensin and one of a proteinase inhibitor or a chemical pathogenicidic or pathogenostatic agent facilitates anti-pathogen activity. The anti-pathogen activity of each of the defensin, proteinase inhibitor and chemical agent is enhanced when the defensin is used in combination with either of the other two agents. In an embodiment, the enhancement results from a synergistic interaction between the defensin and either the proteinase inhibitor or chemical agent.

The pathogen includes a fungus. A fungus includes a yeast. In an embodiment, the pathogen is a human or animal fungal pathogen. Animal including mammalian such as human fungal pathogens include species of *Alternaeria* spp, *Aspergillus* spp, *Candida* spp, *Fusarium* spp, *Trichophyton* spp, *Cryptococcus* spp, *Histoplasma* spp, *Microsporum* spp, *Penicillium* spp, *Pneumocystis* spp *Trichosporon* spp, *Scedosporium* spp, *Paeciliomyces* spp, *Acremonium* spp, *Stachybotrys* spp and Dermatiaceous molds. Specific animal, including mammalian and in particular human pathogens include *Alternaria altemata, Aspergillus fumigatus, Aspergillus niger, Aspergillus flavus, Aspergillus nidulans, Aspergillus paraciticus, Candida albicans, Candida dubliniensis, Candida famata, Candida glabrata, Candida guilliermondii, Candida haemulonii, Candida kefiy, Candida krusei, Candida lusitaniae, Candida norvegensis, Candida parapsilosis, Candida tropicalis, Candida viswanathii, Fusarium oxysporum, Fusarium solani, Fusarium monoliforme, Trychophyton rubrum, Trychophyton mentagrophytes, Trychophyton interdigitales, Trychophyton tonsurans, Cryptococcus neoformans, Cryptococcus gattii, Cryptococcus grubii, Microsporum canis, Microsporum gypseum, Penicillium mameffei, Trichosporon beigelii, Trichosporon asahii, Trichosporon inkin, Trichosporon asteroides, Trichosporon cutaneum, Trichosporon domesticum, Trichosporon mucoides, Trichosporon ovoides, Trichosporon pullulans, Trichosporon loubieri, Trichosporon japonicum, Scedosporium apiospermum, Scedosporium prolificans, Paecilomyces variotii, Paecilomyces lilacinus, Acremonium stricutm, Cladophialophora bantiana, Wangiella dermatitidis, Ramichloridium obovoideum, Chaetomium atrobrunneum, Dactlaria gallopavum, Bipolaris* spp, *Exserohilum rostratum* as well as *Absidia corymbifera, Apophysomyces elegans, Mucor indicus, Rhizomucor pusillus, Rhizopus oryzae, Cunninghamella bertholletiae, Cokeromyces recurvatus, Saksenaea vasiformis, Syncephalastrum racemosum, Basidiobolus ranarum, Conidiobolus coronatuslConidiobolus incongruus, Blastomyces dermatitidis, Coccidioides immitis, Coccidioides posadasii, Histo-* plasma capsula turn, *Paracoccidioides brasiliensis, Pseudallescheria boydii* and *Sporothrix schenckii*.

The defensin and either the proteinase inhibitor or chemical agent may be topically applied to the human or animal or systemically administered to the human or animal. The defensin and/or proteinase inhibitor may also be provided as part of a cellular extract which includes a plant extract. This is useful, for example, in herbal formulations such as body and hair washes.

Further taught herein is a formulation comprising both the defensin and either the proteinase inhibitor or chemical agent or a combination of formulations each comprising one of the defensin or proteinase inhibitor or chemical agent. The formulations are then combined prior to or during use. Reference to a "formulation" includes a cell or plant extract.

Enabled herein is a use of a plant defensin and either the proteinase inhibitor or chemical agent in the manufacture of a medicament for the treatment or prophylaxis of pathogen infestation of a human or animal.

Humans which can be treated include a human of any age. Animals which may be treated include farm animals, companion animals, laboratory test animals and wild animals.

A kit comprising compartments each containing a plant defensin or a functional natural or synthetic derivative or variant thereof, and one or both of a proteinase inhibitor and/or a chemical agent each in separate compartments, is also taught herein. Assays to identify suitable defensins and optimizing concentrations of various components are also contemplated by the present disclosure.

In another embodiment, microorganisms belonging to genera or species of normal flora are genetically engineered to produce a protein such as a defensin and/or a proteinase inhibitor. Such microorganisms may be used as a probiotic to colonize gut regions or skin surface regions which may be used in conjunction with an anti-fungal chemical agent. Alternatively, the defensin and/or proteinase inhibitor is provided as a cell extract including a plant.

TABLE 1

Summary of sequence identifiers

| SEQUENCE ID NO: | DESCRIPTION |
|---|---|
| 1 | Amino acid sequence of C-terminal end amino acid sequence of NaD1 which ends and includes the most C-terminal invariant cysteine residue |
| 2 | A modified amino acid sequence of Class II Solanaceous defensin Loop1B region |
| 3 | A modified amino acid sequence of Class II Solanaceous defensin Loop1B region |
| 4 | A modified amino acid sequence of Class II Solanaceous defensin Loop1B region |
| 5 | A modified amino acid sequence of Class II Solanaceous defensin Loop1B region |
| 6 | A modified amino acid sequence of Class II Solanaceous defensin Loop1B region |
| 7 | Amino acid sequence of Loop1B from NaD1 |
| 8 | Amino acid sequence of HXP4 protein |
| 9 | Amino acid sequence of full length HXL001 protein |
| 10 | Amino acid sequence of full length HXL002 protein |
| 11 | Amino acid sequence of full length HXL004 protein |
| 12 | Amino acid sequence of full length HXL007 protein |
| 13 | Amino acid sequence of full length HXL008 protein |
| 14 | Amino acid sequence of full length HXL013 protein |
| 15 | Amino acid sequence of HXP34 protein |
| 16 | Amino acid sequence of HXP35 protein |
| 17 | Amino acid sequence of HXP37 protein |
| 18 | Amino acid sequence of HXP58 protein |
| 19 | Amino acid sequence of HXP72 protein |
| 20 | Amino acid sequence of HXP91 protein |

TABLE 1-continued

Summary of sequence identifiers

| SEQUENCE ID NO: | DESCRIPTION |
|---|---|
| 21 | Amino acid sequence of HXP92 protein |
| 22 | Amino acid sequence of HXP95 protein |
| 23 | Amino acid sequence of HXP107 protein |
| 24 | Amino acid sequence of full length HXL015 protein |
| 25 | Amino acid sequence of mature HXL012 protein |
| 26 | Amino acid sequence of mature HXL001 protein |
| 27 | Amino acid sequence of mature HXL002 protein |
| 28 | Amino acid sequence of mature HXL004 protein |
| 29 | Amino acid sequence of mature HXL007 protein |
| 30 | Amino acid sequence of mature HXL008 protein |
| 31 | Amino acid sequence of mature HXL013 protein |
| 32 | Amino acid sequence of mature HXL015 protein |
| 33 | Amino acid sequence of mature HXL009 protein |
| 34 | Amino acid sequence of mature HXL035 protein |
| 35 | Amino acid sequence of mature HXL036 protein |
| 36 | Amino acid sequence of mature PhD1A protein |
| 37 | Amino acid sequence of mature NoD173 protein |

DETAILED DESCRIPTION OF THE INVENTION

Throughout this specification, unless the context requires otherwise, the word "comprise" or variations such as "comprises" or "comprising", will be understood to imply the inclusion of a stated element or integer or method step or group of elements or integers or method steps but not the exclusion of any element or integer or method step or group of elements or integers or method steps.

As used in the subject specification, the singular forms "a", "an" and "the" include plural aspects unless the context clearly dictates otherwise. Thus, for example, reference to "a defensin" includes a single defensin, as well as two or more defensins; reference to "an agent" includes a single agent, as well as two or more agents; reference to "the disclosure" includes single and multiple aspects taught by the disclosure; and so forth. Aspects taught and enabled herein are encompassed by the term "invention". All such aspects are enabled within the width of the present invention.

A protocol is developed to facilitate management of pathogen infestation in human and animal subjects. The protocol comprises the use of a plant defensin or a functional natural or synthetic derivative or variant thereof in combination with either a proteinase inhibitor or a chemical pathogenicidic or pathogenostatic agent. It is proposed herein that the plant defensin and the proteinase inhibitor or chemical agent enable an efficacious treatment and prophylaxis protocol against pathogens which infect a human or animal subject. In an embodiment, the effect of the defensin and one or other of the proteinase inhibitor or chemical agent is synergistic.

Hence, enabled herein is a method for inhibiting growth or infestation of a pathogen in a human or animal subject, the method comprising contacting the pathogen with an effective amount of a combination of a plant defensin or a functional natural or synthetic derivative or variant thereof and either: (i) a proteinase inhibitor; or (ii) a chemical pathogenicidic or pathogenostatic agent; in a combined effective amount to inhibit growth or infestation of the pathogen. As indicated above, in an embodiment, the combination of the defensin and the proteinase inhibitor or chemical agent is synergistic compared to the use of each alone at the same individual dose as used in the combination. For convenience, a human and animal subject may also be referred to as a "host", "individual", "target", "recipient" or "patient". The defensin, proteinase inhibitor and chemical entity may each be referred to as an "agent" or collectively as "agents". The agents may be in purified form or comprised within a cell or plant extract. In an embodiment, the chemical entity is added to the cell or plant extract.

In an embodiment, the inhibitory effect of a given defensin, proteinase inhibitor or chemical pathogenicide or pathogenostatic agent alone is significantly enhanced when the defensin is used together with the proteinase inhibitor or the chemical agent. In an embodiment, therefore, the combination is synergistic. Greco et al. (1995) *Pharmacol Rev.* 47:331-385 define a category of synergy on the basis that the use of two agents in combination has greater activity relative to the additive effects when each is assayed alone. Hence, the definition adopted herein includes all such situations provided that the combined effect of the two agents acting together is greater than the sum of the individual agents acting alone. Furthermore, a combination of agents is deemed synergistic, as the term is intended herein, if there exists a set of conditions, including but not limited to concentrations, where the combined effect of the agents acting together is greater than the sum of the individual components acting alone. Richer (1987) *Pestic Sci* 19:309-315 describes a mathematical approach to establish proof of synergy. This approach uses Limpel's formula for comparing an observed level of inhibition (Io) in the combined presence of two inhibitor agents, X and Y, with an expected additive effect (Ee) resulting from each X or Y acting separately at the same respective concentrations as used to measure their combined effect. Additive percent inhibition, Ee, is calculated as X+Y−XY/100 where X and Y are expressed as percent inhibition. Synergism exits where Io>Ee.

Synergy may be expressed as a synergy scale. In an embodiment, a value of up to 15 represents no significant synergy such as 0, 1, 2, 3, 4, 5, 6, 7, 8, 9, 10, 11, 12, 13 or 14; a value of from 15 up to 30 represents low synergy such as 15, 16, 17, 18, 19, 20, 21, 22, 23, 24, 25, 26, 27, 28 or 29; a value of from 30 to 60 represents medium synergy such as 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60; a value greater than 60 represents a high degree of synergy. By "greater than 60" includes from 61 to 100 including 61, 70, 80, 90 and 100 and any value in between.

As indicated above, a "synergistic effect" occurs where two or more agents within the disclosed protocol produce a combined effect that is greater than the sum of the individual effects of each agent acting alone. The effect may be one or more of efficacy, stability, rate, and/or level of toxicity. As described herein, inhibition of pathogen growth is considered synergistic when, measured in the combined presence of at least one plant defensin and at least one of a proteinase inhibitor or a chemical agent is greater than the summed inhibition measured in the presence of a particular concentration range of each agent, defensin and either the proteinase inhibitor or chemical agent, individually, under otherwise identical conditions. It will be understood that it is not necessary that a greater than additive effect be observed with every combination of concentrations of the two agents in order to be deemed synergistic. The synergistic effect of the two agents can be observed under certain concentration combinations, but not in others. For example, if entry into the pathogen limits toxicity, the presence of defensin can result in synergy, especially if the concentration of the proteinase inhibitor or chemical agent is sub-maximal with respect to inhibition. In one embodiment, the concentration of one or both of the defensin and the proteinase inhibitor or chemical agent is sub-maximal. By the same token, synergy can be masked if one or two of the agents is present at such a high level (maximum level) as to result in maximum observable inhibition. The general system for a defensin-proteinase inhibitor/chemical agent combination is, therefore, termed "synergistic" because the potential for synergy is present even if synergy is not observed under all conditions. The synergy between a plant defensin and the proteinase inhibitor or chemical agent provides greater pathogen inhibition than can be obtained by individual agents acting alone, for at least some dosages. In some cases, one of the defensin or other agent is not measurably effective against a particular pathogen until combined with the other. Therefore, the present invention provides for increased protection of a host from pathogen infestation with reduced dependence on antibiotics or chemical agents. This means decreased input cost to the human and animal healthcare system, a broader spectrum of activity against pathogens and reduced potential for spread of resistance.

Hence, in relation to the latter, the selection pressure for development of pathogenicide-resistant pathogen strains is greatly reduced, which allows for an extended commercial life of the agents as well as reduced proliferation of resistant pathogens and reduced likelihood of emergence of multiple-resistant strains of pathogens.

"Pathogen inhibition" includes both pathogenicidic and pathogenostatic activity, as measured by reduction of pathogen growth (or loss of viability) compared to a control. Pathogen growth can be measured by many different methods known in the art depending on the pathogen. A commonly used method of measuring growth of a filamentous fungus, for example, entails germinating spores in a suitable growth medium, incubating for a time sufficient to achieve measurable growth, and measuring increased optical density in the culture after a specified incubation time. The optical density rises with increased growth. Typically, fungal growth is necessary for pathogenesis. Therefore, inhibition of pathogen growth provides a suitable indicator for protection from fungal disease, i.e. the greater the inhibition, the more effective the protection.

"Preventing infection" in the present context, means that the human or animal with the combination of defensin and proteinase inhibitor or chemical agent avoids pathogen infection or disease symptoms or all of the above, or exhibits reduced or minimized or less frequent pathogen infection or disease symptoms or all of the above, that are the natural outcome of the host-pathogen interactions when compared to the host not exposed to the defensin, the combination of the defensin and either the proteinase inhibitor or the chemical agent. That is to say, pathogens are prevented or reduced from causing disease and/or the associated disease symptoms. Infection and/or symptoms are reduced by at least about 10%, 20%, 30%, 40%, 50, 60%, 70% or 80% or greater as compared to a host not so treated with the protocol taught herein. The percentage reduction can be determined by any convenient means appropriate to the host and pathogen.

Hence, the combined action of the defensin and either proteinase inhibitor or chemical agent is to inhibit pathogen growth, replication, infection and/or maintenance, amongst other inhibitory activities and/or induces amelioration of symptoms of pathogen infestation.

Human and animal protection (disease prophylaxis or treatment) can initially be tested using in vitro laboratory assays (e.g. pathogen inhibition assays) followed by animal studies and eventually human clinical trials.

By "contacting" includes exposure of the pathogen to the combination of the defensin and either the proteinase inhibitor or chemical agent following topical or systemic administration or application to the human or animal subject. Hence, the defensin and either the proteinase inhibitor or chemical agent may be applied topically to a surface area on the human or animal subject or they may be systemically administered to the human or animal subject. In addition, some components such as a defensin and/or the proteinase inhibitor can be produced by microorganisms. In another embodiment, microorganisms belonging to genera or species of normal flora are genetically engineered to produce a protein such as a defensin and/or a proteinase inhibitor. Such microorganisms may be used as a probiotic to colonize gut regions or skin surface regions which may be used in conjunction with an anti-fungal chemical agent. Alternatively, the defensin and/or proteinase inhibitor is provided as a cell extract which includes a plant extract. The plant may naturally produce the defensin or proteinase inhibitor or both or it may be engineered to produce one or other or both.

In an embodiment, the defensin and either the proteinase inhibitor or chemical agent are formulated together such as in a topical formulation, hair or body washing solution or a formulation suitable for systemic administration to the appropriate host. Topical formulations include an aqueous solution, a liquid formulation, a tonic, eye drops, ear drops, a wash, a spray, paint, powder, dispersant, an atomized formulation, a douche, cream, ointment, lipstick, gel, sludge, paste, patch, impregnated bandage and the like. A formulation comprising a cell or plant extract comprising a defensin and optionally a proteinase inhibitor is contemplated herein. A fungicide may also be added.

Enabled herein is a formulation comprising a plant defensin or a functional natural or synthetic derivative or variant thereof and either a proteinase inhibitor or chemical pathogenicidic or pathogenostatic agent for use in inhibiting growth or infestation of a pathogen in or on a human or animal subject.

In an embodiment, taught herein is a therapeutic kit comprising multiple compartments wherein a first compartment comprises a plant defensin or a functional natural or synthetic derivative or variant thereof, a second compartment comprises one of proteinase inhibitor or a chemical pathogenicidic or pathogenostatic agent and optionally a third or further compartment comprising excipients, carriers or diluents wherein in use the contents of the first and second compartments are admixed prior to or during application to a human or animal subject or a surface. In an embodiment, all three of a defensin, proteinase inhibitor and a chemical agent are included in separate containers. Alternatively, the kit comprises microorganisms in freeze dried or other reconstructable forms which are engineered to express a defensin and/or a proteinase inhibitor. The kit may then contain a compartment comprising a chemical agent having anti-pathogen properties. The defensin and/or proteinase inhibitor may also be purified from a particular source or is within a plant cell extract.

Described and enabled herein is a defensin or a functional natural or synthetic derivative or variant thereof and either a proteinase inhibitor or chemical agent having anti-pathogen properties for use in inhibiting growth or infestation of a pathogen in or on a human or animal subject, the defensin and other agent being used in combination so as to act to facilitate pathogen inhibition. In an embodiment, the combination is synergistic.

Reference to a "plant defensin" includes a functional natural or synthetic derivative or variant thereof unless the context clearly indicates otherwise. Examples of suitable defensins contemplated herein include permeabilizing defensins, *Solanaceous* Class II defensins and functional natural or synthetic derivatives or variants thereof The defensins used herein may be referred to herein as "naturally occurring" defensin, a "modified" defensin, a "variant" defensin, a "mutated" defensin or a "chimeric" defensin, depending on its source.

In an embodiment, the permeabilizing defensin is a Class II *Solanaceous* defensin. In an embodiment, the defensin is modified at the loop region between the first β-strand (β-strand 1) and the α-helix at the N-terminal end portion of the defensin. In an embodiment, the loop region comprises the 6 amino acids N-terminal of the second invariant cysteine residue or its equivalent. This region is defined as "Loop1B". A Class II Solanaceous defensin is distinguished from other defensins by a relatively conserved C-terminal end portion of the mature domain. Reference to a "Class II *Solanaceous* defensin" includes any defensin having at least 70% amino acid sequence similarity to the C-terminal end portion of the NaD1 mature domain, the C-terminal portion of NaD1 comprising approximately 20 contiguous amino acid residues ending with and including the most C-terminal invariant cysteine in the NaD1 mature domain (for example, SEQ ID NO:1). By "at least 70%" means at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

In an embodiment, the Loop 1B amino acid sequence in a Class II *Solanaceous* defensin is modified to the sequence $X_1 X_2 X_3 X_4 X_5 X_6$ (SEQ ID NO:2) wherein:

$X_1$ is A, R, N, D, C, Q, E, G, H, I, L, K, M, F, P, S, T, W, Y or V or a naturally occurring modified form thereof;

$X_2$ is A, R, N, D, C, Q, E, G, H, I, L, K, M, F, P, S, T, W, Y or V or a naturally occurring modified form thereof;

$X_3$ is A, R, N, D, C, Q, E, G, H, I, L, K, M, F, P, S, T, W, Y or V or a naturally occurring modified form thereof;

$X_4$ is A, R, N, D, C, Q, E, G, H, I, L, K, M, F, P, S, T, W, Y or V or a naturally occurring modified form thereof;

$X_5$ is A, R, N, D, C, Q, E, G, H, I, L, K, M, F, P, S, T, W, Y or V or a naturally occurring modified form thereof; and/or $X_6$ is A, R, N, D, C, Q, E, G, H, I, L, K, M, F, P, S, T, W, Y or V or a naturally occurring modified form thereof; using single letter amino acid nomenclature, wherein the amino acid sequence $X_1 X_2 X_3 X_4 X_5 X_6$ does not correspond to an amino acid sequence of the Loop1B region from the Class II *Solanaceous* defensin prior to modification.

In an embodiment, the Loop1B sequence in a Class II *Solanaceous* defensin is modified to the sequence $X_1 X_2 X_3 X_4 X_5 X_6$ (SEQ ID NO:3) wherein:

$X_1$ is N, G, D, H, K, A, E, Q, T, P, L, M, S, or R;
$X_2$ is K, R, G, H, L, N, F, I, S, T or Y;
$X_3$ is W, Y, H, L, G, F or P;
$X_4$ is P, K, S, R, H, T, E, V, N, Q, D or G;
$X_5$ is S, K, Y, F, G or H; and/or
$X_6$ is P, V, L, T, A, F, N, K, R, M, G, H, I or Y;
wherein the amino acid sequence $X_1 X_2 X_3 X_4 X_5 X_6$ does not correspond to an amino acid sequence of the Loop1B region from the Class II *Solanaceous* defensin prior to modification.

In an embodiment, the Loop 1B sequence in a Class II *Solanaceous* defensin is modified to the sequence $X_1 X_2 X_3 X_4 X_5 X_6$ (SEQ ID NO:4) wherein:

$X_1$ is N, H, Q, D, K or E;
$X_2$ is R, H, T, K or G;
$X_3$ is F, H, Y or W;
$X_4$ is P, K, S or R;

$X_5$ is G or F; and
$X_6$ is P, V, I or N;
wherein the amino acid sequence $X_1$ $X_2$ $X_3$ $X_4$ $X_5$ $X_6$ does not correspond to an amino acid sequence of the Loop1B region from the Class II *Solanaceous* defensin prior to modification.

Reference to "$X_1$ $X_2$ $X_3$ $X_4$ $X_5$ $X_6$" means 6 contiguous amino acid residues corresponding to a Loop 1B region.

In an embodiment, the artificially created or modified defensin comprises the amino acid sequence as set forth in SEQ ID NO:5. In this sequence, the Loop1B region is defined as $X_1$ $X_2$ $X_3$ $X_4$ $X_5$ $X_6$ wherein:

$X_1$ is an amino acid selected from the list consisting of: L, F, S, I, A, H, Y, Q, D, K or G;

$X_2$ is an amino acid selected from the list consisting of: S, V, F, I, K, L, A, P, N, T, R, H or G;

$X_3$ is an amino acid selected from the list consisting of: A, F, W, N, I, S, Y, P, L or H;

$X_4$ is an amino acid selected from the list consisting of: K, G, E, R, A, P, F, Q, V or S;

$X_5$ is an amino acid selected from the list consisting of: M, G, K, D, S, Y, P, E, N or F; and $X_6$ is an amino acid selected from the list consisting of: V, T, M, S, W, A, P, G, E, K, L, H, I or N.

In an embodiment, the artificially created or modified defensin comprises the amino acid sequence as set forth in SEQ ID NO:6. In this sequence, the Loop1B region is defined as $X_1$ $X_2$ $X_3$ $X_4$ $X_5$ $X_6$ wherein:

$X_1$ is an amino acid selected from the list consisting of: N, H, Q, D, K or E;

$X_2$ is an amino acid selected from the list consisting of: R, H, T, K or G;

$X_3$ is an amino acid selected from the list consisting of: F, H, Y or W;

$X_4$ is an amino acid selected from the list consisting of: P, K, S or R;

$X_5$ is an amino acid selected from the list consisting of: G or F; and $X_6$ is an amino acid selected from the list consisting of: P, V, I or N.

In the case of NaD1, a Class II *Solanaceous* defensin, the Loop1B amino acid sequence is NTFPGI (SEQ ID NO:7). Consequently, the NTFPGI is modified such that N is replaced by one of A, R, D, C, Q, E, G, H, I, L, K, M, F, P, S, T, W, Y or V or a naturally occurring modified form thereof; the T is replaced by one of A, R, N, D, C, Q, E, G, H, I, L, K, M, F, P, S, W, Y or V or a naturally occurring modified form thereof; the F is replaced by one of A, R, N, D, C, Q, E, G, H, I, L, K, M, P, S, T, W, Y or V or a naturally occurring modified form thereof; the P is replaced by one of A, R, N, D, C, Q, E, G, H, I, L, K, M, F, S, T, W, Y or V or a naturally occurring modified form thereof; the G is replaced by one of A, R, N, D, C, Q, E, H, I, L, K, M, F, P, S, T, W, Y or V or a naturally occurring modified form thereof; and/or the I is replaced by one of A, R, N, D, C, Q, E, G, H, L, K, M, F, P, S, T, W, Y or V; with the proviso that the Loop1B amino acid sequence does not correspond to the Loop1B from NaD1. The Loop1B sequence may have a single amino acid change or 2 or 3 or 4 or 5 or all 6 amino acids may be altered.

The Class II Solanaceous defensin may be modified by any number of amino acid changes to the Loop1B region alone or in combination with other mutations. Other mutations include amino acid substitutions, additions and/or deletions. Mutations outside the Loop 1B region may number from 1 to about 50. A "change" includes a graft of a Loop1B region from one defensin onto a Class II *Solanaceous* defensin Loop 1B region. The source may be a Class I defensin Loop1B or a Loop1B from another Class II defensin. These aspects are based on the proviso that the enhanced anti-pathogen activity of the combined use of the modified defensin and other agent against at least one human or animal pathogen is maintained. In an embodiment, the anti-pathogen activity is enhanced relative to the Class II defensin prior to modification in terms of level or spectrum of activity, stability and/or permeabilization. In an embodiment, the anti-pathogen activity is enhanced relative to the peptide prior to modification of the Class II defensin in terms of level or spectrum of activity, stability and/or permeabilization.

Hence, included herein is the use of a proteinase inhibitor or a chemical agent with anti-pathogen properties with an artificially created defensin comprising a modified Class II *Solanaceous* defensin backbone wherein the loop region between n-strand 1 and the α-helix on the N-terminal end portion is modified by a single or multiple amino acid substitution, addition and/or deletion to generate a variant defensin which has anti-pathogen activity. In an embodiment, the loop region is Loop 1B defined by the 6 amino acid residues N-terminal to the second invariant cysteine residue. Its equivalent region in any defensin is contemplated herein.

Examples of suitable defensins include NaD1, TPP3, PhD1, PhD1A, PhD2, FST, NoD173, HXL001 (SEQ ID NO:26), HXL002 (SEQ ID NO:27), HXL004 (SEQ ID NO:28), HXL007 (SEQ ID NO:29), HXL008 (SEQ ID NO:30), HXL009 (SEQ ID NO:33) HXL012 (SEQ ID NO:25) HXL013 (SEQ ID NO:31), HXL015 (SEQ ID NO:32) , HXL035 and HXL036. Examples of synthetic defensin variants include HXP4 (SEQ ID NO:8), HXP34 (SEQ ID NO:15) and HXP35 (SEQ ID NO:16). Other examples of variant defensins include HXP37 (SEQ ID NO:17), HXP58 (SEQ ID NO:18), HXP72 (SEQ ID NO:19), HXP91 (SEQ ID NO:20), HXP92 (SEQ ID NO:21), HXP95 (SEQ ID NO:22) and HXP107 (SEQ ID NO:23).

Taught herein is a method for inhibiting growth or infestation of a pathogen, the method comprising contacting the pathogen with an effective amount of a combination of a plant defensin selected from the list consisting of NaD1, TPP3, PhD1, PhD1A, PhD2, FST, NoD173, HXL001, HXL002, HXL004, HXL007, HXL008, HXL009, HXL012, HXL013, HXL015, HXL035 and HXL036 or a variant or derivative of a defensin selected from the list consisting of HXP4, HXP34, HXP35, HXP37, HXP58, HXP72, HXP91, HXP92, HXP95 and HXP107 and a proteinase inhibitor or chemical agent having anti-pathogen properties, the combination of the defensin and either a proteinase inhibitor or chemical agent facilitates anti-pathogen activities compared to the use of each alone at the same individual dose as used in the combination.

In an embodiment, the agents act in synergy.

Suitable proteinase inhibitors include serine and cysteine proteinase inhibitors such as NaPI, NaCys1, NaCys2, NaCys3, NaCys4, HvCPI6, SlCys9, Oc-Ia, Oc-Ib, Oc-Ic, Oc-Id, StPin1A, At2g38870, CI-1B, CI-2, At2g43510 and BPTI.

Reference to a "chemical agent" includes a proteinaceous and non-proteinaceous chemical molecule. Chemical pathogenicidic or pathogenistatic agents include a fungicide selected from the list consisting of ciclopirox, terbinafine, fenpropimorph, ketoconazole, intraconazole, fluconazole, amorolfine, amphotericin, azole, polyene, echinocandin, allylamine, griseofulvin, tolnaftate, benzoxaborole, aganocide, flucytosine, haloprogin, polygodial and undecylenic acid. An example of an echinocandin fungicide is caspofungin. Chemical cell wall synthase inhibitors are also contemplated herein. Proteinaceous pathogenicidic or pathogenistatic agents include a β-glucan synthase inhibitor and a chitin synthase inhibitor as well as other cell wall synthase inhibitors.

Taught herein is a method for inhibiting growth or infestation of a pathogen, the method comprising contacting the pathogen with an effective amount of combination of a plant defensin selected from the list consisting of NaD1, TPP3, PhD1, PhD1A, PhD2, FST, NoD173, HXL001, HXL002, HXL004, HXL007, HXL008, HXL009, HXL012, HXL013, HXL015, HXL035 and HXL036 or a variant or derivative of a defensin selected from the list consisting of HXP4, HXP34, HXP35, HXP37, HXP58, HXP72, HXP91, HXP92, HXP95 and HXP107 and either a proteinase inhibitor selected from the list consisting of NaPI, NaCys1, NaCys2, NaCys3, NaCys4, HvCPI6, SlCys9, Oc-Ia, Oc-Ib, Oc-Ic, Oc-Id, StPin1A, At2g38870, CI-1B, CI-2, At2g43510 and BPTI or a chemical agent selected from the list consisting of ciclopirox, terbinafine, fenpropimorph, ketoconazole, intraconazole, fluconazole, amorolfine, amphotericin, an azole, a polyene, an echinocandin (e.g. caspofungin), an allylamine, griseofulvin, tolnaftate, benzoxaborole, aganocide, flucytosine, haloprogin, polygodial, undecylenic acid, a β-glucan synthase inhibitor and a chitin synthase inhibitor the combination of the defensin and the other agent facilitates anti-pathogen activity compared to the use of each alone at the same individual dose as used in the combination. In an embodiment, the combination is synergistic.

In an embodiment the pathogen is a fungus.

Taught herein is a method for inhibiting growth or infestation of a fungal pathogen, the method comprising contacting the fungal pathogen with an effective amount of combination of a plant defensin selected from the list consisting of NaD1, TPP3, PhD1, PhD1A, PhD2, FST, NoD173, HXL001, HXL002, HXL004, HXL007, HXL008, HXL009, HXL012, HXL013, HXL015, HXL035 and HXL036 or a variant or derivative of a defensin selected from the list consisting of HXP4, HXP34, HXP35, HXP37, HXP58, HXP72, HXP91, HXP92, HXP95 and HXP107 and either a proteinase inhibitor selected from the list consisting of NaPI, NaCys1, NaCys2, NaCys3, NaCys4, HvCPI6, SlCys9, Oc-Ia, Oc-Ib, Oc-Ic, Oc-Id, StPin1A, At2g38870, CI-1B, CI-2, At2g43510 and BPTI or a chemical agent selected from the list consisting of ciclopirox, terbinafine, fenpropimorph, ketoconazole, intraconazole, fluconazole, amorolfine, amphotericin, an azole, a polyene, an echinocandin (e.g. caspofungin), an allylamine, griseofulvin, tolnaftate, benzoxaborole, aganocide, flucytosine, haloprogin, polygodial, undecylenic acid, a β-glucan synthase inhibitor and a chitin synthase inhibitor in a combination of the defensin and the other agent which facilitates inhibition or growth of the pathogen. In an embodiment, the combination is synergistic.

The present method is useful in the treatment or prophylaxis of a subject. The term "subject" includes a human of any age or an animal such as a farm animal (e.g. sheep, pig, horse, cow, donkey, llama, alpaca or poultry bird (e.g. chicken, duck, turkey, pheasant, peacock)), companion animal (e.g. dog or cat), laboratory test animal (e.g. mouse, rat, rabbit, guinea pig or hamster) or captive wild animal (e.g. kangaroo, Tasmanian devil or wild feline animal). A "human" or "animal" includes a part thereof such as fingers, toes, nails, eyes, ears, mouth, nose, sinuses, hooves, reproductive tissues, lungs, skin and scalp.

Animal including mammalian such as human fungal pathogens include species of *Alternaeria* spp, *Aspergillus* spp, *Candida* spp, *Fusarium* spp, *Trichophyton* spp, *Cryptococcus* spp, *Histoplasma* spp, *Microsporum* spp, *Penicillium* spp, *Pneumocystis* spp *Trichosporon* spp, *Scedosporium* spp, *Paecihomyces* spp, *Acremonium* spp, *Stachybotrys* spp and Dermatiaceous molds. Specific animal, including mammalian and in particular human pathogens include *Alternaria alternata, Aspergillus fumigatus, Aspergillus niger, Aspergillus flavus, Aspergillus nidulans, Aspergillus paraciticus, Candida albicans, Candida dubliniensis, Candida famata, Candida glabrata, Candida guilliermondii, Candida haemulonii, Candida kefiy, Candida krusei, Candida lusitaniae, Candida norvegensis, Candida parapsilosis, Candida tropicalis, Candida viswanathii, Fusarium ozysporum, Fusarium solani, Fusarium monoliforme, Trychophyton rubrum, Trychophyton mentagrophytes, Trychophyton interdigitales, Trychophyton tonsurans, Cryptococcus neoformans, Cryptococcus gattii, Cryptococcus grubii, Microsporum canis, Microsporum gypseum, Penicillium marneffei, Trichosporon beigelii, Trichosporon asahii, Trichosporon inkin, Trichosporon asteroides, Trichosporon cutaneum, Trichosporon domesticum, Trichosporon mucoides, Trichosporon ovoides, Trichosporon pullulans, Trichosporon loubieri, Trichosporon japonicum, Scedosporium apiospermum, Scedosporium prohjicans, Paecilomyces variotii, Paecilomyces lilacinus, Acremonium stricutm, Cladophialophora bantiana, Wangiella dermatitidis, Ramichloridium obovoideum, Chaetomiurn atrobrunneum, Dactlaria gallopavum, Bipolaris* spp, *Exserohilum rostratum* as well as *Absidia corymbifera, Apophysomyces elegans, Mucor indicus, Rhizomucor pusillus, Rhizopus oryzae, Cunninghamella bertholletiae, Cokeromyces recurvatus, Saksenaea vasiformis, Syncephalastrum racemosum, Basidiobolus ranarum, Conidiobolus coronatus/Conidiobolus incongruus, Blastomyces dermatitidis, Coccidioides immitis, Coccidioides posadasii, Histoplasma capsulatum, Paracoccidioides brasiliensis, Pseudallescheria boydii* and *Sporothrix schenckii.*

The combination of the defensin and either the proteinase inhibitor or chemical agent taught herein is useful for combating pathogen diseases or infection in humans and animals. Hence, the subject specification teaches a protocol for the treatment or prophylaxis of pathogens. The protocol has human and veterinary applications. Further provided is a process of combating pathogens whereby they are exposed to the combination of a defensin and either a proteinase inhibitor or a chemical agent having anti-pathogen properties herein described. One or both of the defensins and/or peptide may be used in the form of a composition.

Another aspect taught herein is a composition comprising a plant defensin or a functional natural or synthetic derivative or variant thereof and either a proteinase inhibitor or a chemical agent having anti-pathogen properties together with one or more pharmaceutically or veterinary acceptable carriers, diluents or excipients. In another embodiment, two compositions are used, one comprising the defensin and one comprising the other agent. In an embodiment, the composition is in the form of a spray, mist, micro- or nano-particles, an aqueous solution, a wash, a tonic, a dispersant, an atomized formulation, douche, lipstick, sludge, powder, cream, ointment, gel, patch, impregnated bandage, liquid, formulation, paint or other suitable distribution medium including topical or systemic forms of the composition. By "systemic form" includes a form suitable or oral, intravenous intra peripheral, subcutaneous, intrathecal, intracranial, vaginal or rectal administration. A composition includes a cell or plant extract comprising one or other or both of a defensin and/or proteinase inhibitor. A chemical agent may be added to the composition.

For compositions comprising the defensin and the other agent described herein, generally include a carrier, excipient, diluent, preservative, stabilizer and/or a solid or liquid additive.

The composition may take a wide variety of forms depending on the intended method of administration. Generally, but not exclusively, topical compositions are used for human or animal subjects. In preparing the compositions, usual media may be employed such as, for example, water, glycols, oils, alcohols, preservatives and/or coloring agents. The compositions may take the form of a liquid preparation such as, for example, suspensions, elixirs and solutions. Carriers such as starches, sugars, microcrystalline cellulose, diluents, granulating agents, lubricants, binders, disintegrating agents and the like may also be used. The composition may also be in the form of a powder, capsule and tablet.

When administered by aerosol or spray, the compositions are prepared according to techniques well-known in the art of pharmaceutical formulation and may be prepared as solutions in saline, employing benzyl alcohol or other suitable preservatives, absorption promoters to enhance bioavailability, fluorocarbons and/or other solubilizing or dispersing agents known in the art.

The effective dosage of the defensin and other agent may vary depending on the particular combination employed, the mode of administration, the pathogen being treated and the severity of the pathogen infestation. Thus, the dosage regimen utilizing the defensin and peptide is selected in accordance with a variety of factors including type, species, age, weight, sex and medical condition of the subject; the severity of the condition to be treated; the route of administration; and the particular defensin thereof employed. A physician, clinician or veterinarian of ordinary skill can readily determine and, if necessary, prescribe the effective amount of the defensin required to prevent, counter or arrest the progress of Dragee cores are provided with suitable coatings. For this purpose, concentrated sugar solutions may be used, which may optionally contain gum arabic, talc, polyvinyl pyrrolidone, carbopol gel, polyethylene glycol and/or titanium dioxide, lacquer solutions, and suitable organic solvents or solvent mixtures. Dyestuffs or pigments may be added to the tablets or dragee coatings for identification or to characterize different combinations of active compound doses.

Defensin-agent preparations include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In another embodiment, microorganisms belonging to genera or species of normal flora are genetically engineered to produce a protein such as a defensin and/or a proteinase inhibitor. Such microorganisms may be used as a probiotic to colonize gut regions or skin surface regions which may be used in conjunction with an anti-fungal chemical agent. Alternatively, the defensin and/or proteinase inhibitor is provided as a cell extract.

Another aspect provides a protocol or method for treating or preventing an animal including a mammalian such as a human subject from being infected or infested with a pathogen, the protocol or method comprising applying to the subject an anti-pathogen effective amount of a composition comprising the plant defensin and either a proteinase inhibitor or a chemical agent having anti-pathogen properties as described herein.

The term "applying" includes contacting and exposing.

The present defensin and peptide may be manufactured based on its amino acid sequence using standard stepwise addition of one or more amino acid residues using, for example, a peptide or protein synthesizer. Alternatively, the defensin and peptide may be made by recombinant means or is purified from a natural source or is in an extract from a plant or other biological source. For example, extracts may be used in a body wash or shampoo.

As indicated above, the combination of the defensin and other agent exhibits improved or enhanced anti-pathogen activity.

Still another aspect provides a method for reducing or controlling pathogen infestation on or in a human or animal subject the method comprising topically applying a combination of a plant defensin and either a proteinase inhibitor or chemical agent having anti-pathogen properties to a potentially infected surface region on the human or animal. Hence, animal and in particular mammalian such as human anti-pathogen medicaments are contemplated herein. In an embodiment, the medicament is in the form of a powder, spray, atomizer, nanoparticle, gel, paste, impregnated bandage, paint, aerosol, drench or other liquid. The anti-pathogen formulation may also be a slow release composition. The formulation may be used to treat an infected subject or as a preventative. In an example, the formulation is used to prevent or treat fungal infection or infestation of nails, scalp, eyes, ears, nose sinuses, hooves, reproductive tissues, lungs, and skin areas such as between toes.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The present disclosure illustratively described herein suitably may be practiced in the absence of any element or elements, limitation or limitations which is not specifically disclosed herein.

When a Markush group or other grouping is used herein, all individual members of the group and all combinations and subcombinations possible of the group are intended to be individually included in the disclosure.

When a range is recited herein, it is intended that all subranges within the stated range, and all integer values within the stated range, are intended, as if each subrange and integer value was recited.

Once a permeabilizing defensin is identified together with the concentration range providing optimal permeabilization, it is tested with different combinations of peptides against selected pathogens.

EXAMPLES

Aspects disclosed and enabled herein are now described in the following non-limiting Examples.

Methods

Purification of Defensins from *Pichia pastoris*

A single pPINK-defensin *P. pastoris* PichiaPink (Trademark) strain 1 colony is used to inoculate 25 mL of BMG medium (described in the Invitrogen *Pichia* Expression Manual) in a 250 mL flask and that is incubated over for 2-3 days in a 30° C. shaking incubator (140 rpm). The culture is used to inoculate 200 mL of BMG in a 1 L baffled flask which is placed in a 30° C. shaking incubator (140 rpm) overnight. The cells are harvested by centrifugation (2,500× g, 10 min, 4° C.) and resuspended into 1 L of BMM medium in a 5 L baffled flask and incubated in a 28° C. shaking incubator for 3 days. The cultures are induced at t=24 and 48 h. The expression medium is separated from cells by centrifugation (6000 rpm, 20 minutes). The medium is adjusted to pH 3.0 before it is applied to an SP Sepharose column (1 cm×1 cm, Amersham Biosciences) pre-equilibrated with 100 mM potassium phosphate buffer, pH 6.0. The column is then washed with 100 mL of 100 mM potassium phosphate buffer, pH 6.0 and bound protein is eluted in 10×10 mL of 100 mM potassium phosphate buffer containing 500 mM NaCl. Eluted proteins are concentrated down to 1 mL using a centrifugal column and washed 5× using sterile milli Q ultrapure water. The protein concentration of Pichia-expressed defensin is determined using the bicinchoninic acid (BCA) protein assay (Pierce Chemical Co.) with bovine serum albumin (BSA) as the protein standard.

Preparation of Proteinase Inhibitors

Total RNA was extracted from tomato (Solanum lycopersicum) leaf using the RNeasy Plant Mini Kit (Qiagen). cDNA was then synthesized using SuperScript II Reverse Transcriptase (Life Technologies). DNA encoding the mature form of SlCys9 (Genbank accession number AF198388) without the C-terminal extension (previously designated tSlCys9 (Girard et al. (2007) *New Phytol* 173: 841-851) but here referred to as SlCys9N) was amplified and inserted into the pHUE expression vector (Cantanzariti et al. (2004) *Protein Science* 13:1331-1339) using Sac II and Sac I. For HvCPI6, genomic DNA was extracted from barley (Hordeum vulgare) leaf using the Dneasy Plant Mini Kit (Qiagen). DNA encoding the mature form of HvCPI6 (Genbank accession number AJ748341) was amplified and inserted into the pHUE expression vector (Cantanzariti et al (2004) supra) using Sac II and Sac I. Plasmid DNA was isolated and then used to transform *E. coli* Tuner (DE3) pLysS (Novagen) cells.

Single colonies of *E. coli* Tuner (DE3) pLysS (Novagen) were used to inoculate 2YT media (10 mL, 16 g/L tryptone, 10 g/L yeast extract, 5 g/L NaCl) containing ampicillin (0.1 mg/mL), chloramphenicol (0.34 mg/mL), tetracycline (0.1 mg/mL) and kanamycin (0.015 mg/mL) and grown overnight with shaking at 37° C. This culture was used to inoculate 2YT media (500 mL) containing ampicillin (0.1 mg/mL), chloramphenicol (0.34 mg/mL), tetracycline (0.1 mg/mL) and kanamycin (0.015 mg/mL) which was then grown for 4 hours to an optical density (600 nm) of ~1.0. IPTG was then added (0.5 mM final concentration) and the culture grown for a further 4 hours at 37° C. Cells were harvested by centrifugation (4,000 g at 4° C. for 20 minutes), resuspended in native lysis buffer (20 mL per litre cell culture, 50 mM $NaH_2PO_4$, 300 mM NaCl, 10 mM imidazole, pH 8.0) and frozen at −80° C. Cells were then thawed and treated with lysozyme (5 mg per 25 mL resuspended cells) for 20 minutes at 4° C. DNase I (125 uL, 2 mg/mL in 20% glycerol, 75 mM NaCl) and $MgCl_2$ (125 uL, 1 M) were then added and the samples incubated at room temperature for 40 minutes on a rocking platform. The samples were then sonicated for 2×30 s on ice (80% power, Branson sonifier 450) and centrifuged (20,000 g at 4° C. for 30 minutes). The hexahistidine-tagged ubiquitin-fusion proteins (His6-Ub-SlCys9N/HVCP16) were then purified from the protein extracts by immobilized metal affinity chromatography (IMAC) under native conditions using Ni-NTA resin (1.5 mL to ~25 mL native protein extract, Qiagen) according to the manufacturer's instructions. Recombinant proteins were eluted using elution buffer (250 mM imidazole, 200 mM NaCl, 50 mM $NaH_2PO_4$, pH 8.0). The imidazole was removed by applying the eluted protein to a prepacked Sephadex G50 gel filtration column (PD-10, Amersham) equilibrated with 50 mM Tris.Cl, 100 mM NaCl, pH 8.0.

The hexahistidine-tagged ubiquitin was cleaved from the recombinant proteins using the deubiquitylating enzyme 6H.Usp2-cc (Catanzariti et al. (2004) *Protein Sci* 13:1331-1339). The cleaved tag was removed by another round of IMAC with the de-ubiquitylated protease inhibitors as the unbound protein. This was then further purified by reversed-phase HPLC.

Recombinant HvCPI6 and SlCys9N were prepared as 10 times stock solutions in $H_2O$. Bovine pancreatic trypsin inhibitor (BPTI) was purchased from Sigma (product number T0256) and diluted to a 10 times stock solution in $H_2O$.

Preparation of Chemical Fungicides

Chemical fungicides were sourced commercially and were prepared as 10× stock solutions in $H_2O$ (caspofungin and fenpropimorph) or as a 100× stock in methanol (terbinafine).

Preparation of Spores

Spores are isolated from sporulating fungus spp. growing on yeast extract peptone dextrose agar (*Candida albicans, Cryptococcus gattii*—1.5×10$^6$) or ½ strength Sabouraud dextrose agar (*Trichophyton interdigitale, Microsporum fulvum*—5×10$^4$). Spores are removed from the plates by the addition of ½ strength potato dextrose broth (PDB). Spore concentrations are measured using a haemocytometer.

Antifungal assays

Antifungal assays were conducted in 96 well microtitre plates. Wells were loaded with 10 μL of filter sterilized (0.22 μm syringe filter, Millipore) defensin (10× stock for each final concentration) or water, 10 μL, of filter sterilized (0.22 μm syringe filter, Millipore) proteinase inhibitor or chemical fungicide (10× stock for each final concentration) or water and 80 μL of 5×10$^3$ spores/mL in ½ strength PDB. The plates were incubated at 24° C. Fungal growth was assayed by measuring optical density at 595 nm (A595) using a microtitre plate reader (SpectraMax Pro M2; Molecular Devices. Growth was allowed to proceed until the optical density (OD) of the fungus in the absence of any test defensin reached an OD of 0.2. Each test was performed in duplicate.

Synergy is classified as the difference between the observed % fungal growth inhibition caused by the combination of a defensin and a proteinase inhibitor (or a defensin and a chemical fungicide) (Io value) and the expected % fungal growth inhibition of the defensin and the proteinase inhibitor (or the defensin and the chemical fungicide) based on the sum of the % fungal growth inhibition of the defensin and the proteinase inhibitor (or the defensin and the chemical fungicide) on their own (Ee value calculated according to the Limpel formula used by Richer et al. (1987) supra). The difference, Io-Ee, is the synergy value. A synergy value up to 15 means no significant synergy; 15-30 is a low level of synergy; 30-60 is a medium level of synergy; and >60 is a high level of synergy. Synergy calculations are presented in Tables 2 through 7 wherein, as indicated above, Ee is the expected effect from the additive response according to Limpel's formula expressed as percent inhibition and To is the percent inhibition observed. Synergy occurs when To values are higher than Ee values.

Example 1

Permeabilizing Defensin and Proteinase Inhibitor

Defensins include a Solanaceous Class II defensin (NaD1), an artificial variant (HXP4) and Class I defensins (HXL001, HXL004, HXL008, HXL012, HXL013, HXL015) which are permeabilizing defensins. These are partnered with the proteinase inhibitors BPTI, HvCPI6 or SlCys9N. The results are shown in Tables 2 to 5.

The results of synergistic inhibition of *Candida albicans* are shown in Table 2.

TABLE 2

*Candida albicans*

| Permeabilizing defensin | Proteinase Inhibitor | Expected inhibition | Observed inhibition | Synergy |
|---|---|---|---|---|
| NaD1 (2 µM) | BPTI (0.625 µM) | 29.7 | 94.1 | 64.4 |
| | HyCPI6 (2.5 µM) | 0.0 | 64.7 | 64.7 |
| | SlCys9N (2.5 µM) | 31.9 | 94.8 | 62.9 |
| HXP4 (2 µM) | BPTI (0.625 µM) | 16.2 | 100 | 83.8 |
| | HyCPI6 (2.5 µM) | 15.9 | 93.5 | 77.6 |
| | SlCys9N (2.5 µM) | 33 | 92.4 | 59.4 |
| HXL001 (4 µM) | BPTI (0.625 µM) | 2.6 | 72.6 | 70.1 |
| | HyCPI6 (2.5 µM) | 59.2 | 84.2 | 25.0 |
| | SlCys9N (2 µM) | 68.1 | 85.0 | 16.9 |
| HXL004 (2 µM) | BPTI (0.625 µM) | 9.6 | 91.2 | 81.6 |
| | HyCPI6 (2.5 µM) | 63.6 | 93.5 | 29.9 |
| | SlCys9N (2.5 µM) | 55.2 | 81.8 | 26.6 |
| HXL008 (2 µM) | BPTI (0.625 µM) | 0.0 | 100.0 | 100.0 |
| | HyCPI6 (2.5 µM) | 14.8 | 63.8 | 49.0 |
| | SlCys9N (2.5 µM) | 30.2 | 98.9 | 68.7 |
| HXL012 (4 µM) | BPTI (0.625 µM) | 14.8 | 89.7 | 74.9 |
| | HyCPI6 (2.5 µM) | 12.3 | 100.0 | 87.7 |
| | SlCys9N (2.5 µM) | 34.5 | 97.3 | 62.8 |
| HXL013 (1 µM) | HyCPI6 (2.5 µM) | 10.1 | 100.0 | 89.9 |
| | SlCys9N (2.5 µM) | 13.8 | 100.0 | 86.2 |
| HXL015 (1 µM) | BPTI (0.625 µM) | 28.1 | 100.0 | 71.9 |
| | HyCPI6 (2.5 µM) | 0.0 | 100.0 | 100.0 |
| | SlCys9N (2.5 µM) | 0.0 | 94.7 | 94.7 |

The results of synergistic inhibition of *Cryptococcus gattii* are shown in Table 3.

TABLE 3

*Cryptococcus gattii*

| Permeabilizing defensin | Proteinase Inhibitor | Expected inhibition | Observed inhibition | Synergy |
|---|---|---|---|---|
| NaD1 (2 µM) | BPTI (0.625 µM) | 22.0 | 95.6 | 73.7 |
| | HvCPI6 (2.5 µM) | 32.1 | 96.2 | 64.1 |
| | SlCys9N (2.5 µM) | 0.0 | 98.8 | 98.8 |
| HXP4 (0.5 µM) | BPTI (0.625 µM) | 48.8 | 97.4 | 48.6 |
| | HvCPI6 (2.5 µM) | 18.6 | 97.4 | 78.8 |
| | SlCys9N (2.5 µM) | 0.0 | 99.3 | 99.3 |

The results of synergistic inhibition of *Trichophyton interdigitale* are shown in Table 4.

TABLE 4

*Trichophyton interdigitale*

| Permeabilizing defensin | Proteinase Inhibitor | Expected inhibition | Observed inhibition | Synergy |
|---|---|---|---|---|
| NaD1 (1 µM) | BPTI (0.625 µM) | 57.9 | 89.1 | 31.2 |
| | HvCPI6 (2.5 µM) | 33.5 | 71.6 | 38.1 |
| | SlCys9N (2.5 µM) | 28.1 | 81.1 | 53.0 |
| HXP4 (0.5 µM) | BPTI (0.625 µM) | 32.9 | 69.0 | 36.1 |
| | HvCPI6 (2.5 µM) | 31.1 | 56.8 | 25.7 |
| | SlCys9N (2.5 µM) | 9.7 | 53.0 | 43.4 |
| HXL001 (0.5 µM) | BPTI (0.625 µM) | 36.9 | 67.4 | 30.5 |
| | HvCPI6 (2.5 µM) | 32.5 | 84.7 | 52.2 |
| | SlCys9N (2.5 µM) | 16.8 | 70.2 | 53.4 |

The results of synergistic inhibition of *Microsposum fulvum* are shown in Table 5.

TABLE 5

*Microsposum fulvum*

| Permeabilizing defensin | Proteinase Inhibitor | Expected inhibition | Observed inhibition | Synergy |
|---|---|---|---|---|
| NaD1 (0.5 µM) | BPTI (0.625 µM) | 34.3 | 52.9 | 18.6 |
| | HyCPI6 (0.625 µM) | 19.0 | 43.8 | 24.8 |
| | SlCys9N (5 µM) | 40.7 | 79.9 | 39.2 |

Example 2

Permeabilizing Defensin and Fungicide

Defensins include a *Solanaceous* Class II defensin (NaD1), an artificial variant (HXP4) and Class I defensins (HXL001, HXL002, HXL004, HXL008, HXL009, HXL012, HXL013, HXL015) which are permeabilizing defensins. These are partnered with the chemical fungicides caspofungin, fenpropimorph and terbinafine.

The results for synergistic inhibition of *Candida albicans* is shown in Table 6.

TABLE 6

*Candida albicans*

| Fungicide | Permeabilizing defensin | Expected inhibition | Observed inhibition | Synergy |
|---|---|---|---|---|
| Caspofungin (2 ng/ml) | NaD1 (1 µM) | 1.2 | 61.7 | 60.5 |
| | HXL004 (1 µM) | 14.0 | 92.3 | 78.3 |
| | HXL013 (1 µM) | 4.3 | 90.8 | 86.5 |
| | HXP4 (1.5 µM) | 14.5 | 64.5 | 50.0 |
| Caspofungin (4 ng/ml) | HXL001 (2.5 µM) | 11.7 | 73.4 | 61.7 |
| | HXL002 (2.5 µM) | 6.1 | 40.8 | 34.7 |
| | HXL009 (2.5 µM) | 3.7 | 65.2 | 61.5 |
| | HXL012 (2.5 µM) | 0 | 51.2 | 51.2 |
| Fenpropimorph (2 ug/ml) | HXP4 (1.5 µM) | 15 | 97.6 | 82.6 |
| | HXL008 (2 µM) | 46.7 | 87.3 | 40.6 |
| | HXL015 (1 µM) | 19 | 71.8 | 52.8 |
| Terbinafine (4 ng/ml) | HXP4 (1.5 µM) | 44.8 | 82.7 | 37.9 |

Example 3

Non-permeabilizing Defensin and Fungicide

Table 7 shows the no to low synergy when a non-permeabilizing defensin is used.

TABLE 7

Candida albicans

| Fungicide | Non-permeabilizing defensin | Expected inhibition | Observed inhibition | Synergy |
|---|---|---|---|---|
| Caspofungin (2 ng/ml) | DmAMP1 (1 µM) | 18.5 | 30.0 | 11.5 |
| | RsAFP2 (1 µM) | 1.7 | 19.0 | 17.3 |

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

BIBLIOGRAPHY

Bloch and Richardson (1991) *FEBS Lett* 279(1):101-104
Bevan etal. (1983) *Nucleic Acids Res* 11(2):369-385
Catanzariti et al. (2004) *Protein Sci* 13:1331-1339
Colilla etal. (1990) *FEBS Lett* 270(1-2):191-194
Girard etal. (2007) *New Phytol* 173:841-851
Greco etal. (1995) *Pharmacol Rev.* 47:331-385
Herrera-Estrella etal. (1983) *EMBO J* 2:987-995
Janssen etal. (2003) *Biochemistry* 42(27):8214-8222
Klee et al. (1985) *Bio/Technology* 3:637-642
Lay et al. (2003) *Plant Physiol* 131(3):1283-1293
Nilsson etal. (1989) *Cell* 58:707
Richer (1987) *Pestic Sci* 19:309-315
Spelbrink etal. (2004) *Plant Physiol* 135(4):2055-2067
van der Weerden etal. (2008) *J Biol Chem* 283(21):14445-14452
Yount and Yeaman (2005) *Protein Pept Lett* 12(1):49-67

What is claimed is:

1. A method for inhibiting growth or infestation of a pathogen in or on a human or animal subject, said method comprising contacting the pathogen with an effective amount of a combination of a plant defensin and a chemical pathogenicidic or pathogenostatic agent in a combined amount effective to inhibit growth or infestation of the pathogen, wherein the plant defensin is a Class I defensin or a *Solanaceous* Class II defensin, wherein the combination of the defensin and the chemical pathogenicidic or pathogenostatic agent exhibits synergistic effect of inhibition compared to use of each alone at the same individual dose as used in the combination, wherein the chemical pathogenicidic or pathogenostatic agent is a β-glucan synthase inhibitor, wherein the pathogen is a fungal pathogen selected from the group consisting of *Alternaeria* spp, *Aspergillus* spp, *Candida* spp, *Fusarium* spp, *Trichophyton* spp, *Cryptococcus* spp, *Histoplasma* spp, *Microsporum* spp, *Penicillium* spp, *Pneumocystis* spp, *Trichosporon* spp, *Scedosporium* spp, *Paecilomyces* spp, *Acremonium* spp, *Stachybotrys* spp and Dematiaceous molds, and wherein the Class I defensin and the *Solanaceous* Class II defensin do not comprise a synthetic derivative or variant thereof.

2. The method of claim 1, wherein the plant defensin is a permeabilizing defensin.

3. The method of claim 2, wherein the permeabilizing defensin is selected from the group consisting of TPP3, PhD1, PhD1A, PhD2, FST, NoD173, HXL001, HXL002, HXL004, HXL007, HXL008, HXL009, HXL012, HXL013, HXL015, HXL035 and HXL036.

4. The method of claim 1, wherein the β-glucan synthase inhibitor is an echinocandin.

5. The method of claim 4, wherein the echinocandin is caspofungin.

6. The method of claim 1, wherein the fungal pathogen is selected from the group consisting of *Alternaria alternata, Aspergillus fumigatus, Aspergillus niger, Aspergillus flavus, Aspergillus nidulans, Aspergillus paraciticus, Candida albicans, Candida dubliniensis, Candida famata, Candida glabrata, Candida guilliermondii, Candida haemulonii, Candida kefyr, Candida krusei, Candida lusitaniae, Candida norvegensis, Candida parapsilosis, Candida tropicalis, Candida viswanathii, Fusarium oxysporum, Fusarium solani, Fusarium moniliforme, Trichophyton rubrum, Trichophyton mentagrophytes, Trichophyton interdigitales, Trichophyton tonsurans, Cryptococcus neoformans, Cryptococcus gattii, Cryptococcus grubii, Microsporum canis, Microsporum gypseum, Penicillium marneffei, Trichosporon beigelii, Trichosporon asahii, Trichosporon inkin, Trichosporon asteroides, Trichosporon cutaneum, Trichosporon domesticum, Trichosporon mucoides, Trichosporon ovoides, Trichosporon pullulans, Trichosporon loubieri, Trichosporon japonicum, Scedosporium apiospermum, Scedosporium prolificans, Paecilomyces variotii, Paecilomyces lilacinus, Acremonium stricutm, Cladophialophora bantiana, Wangiella dermatitidis, Ramichloridium obovoideum, Chaetomium atrobrunneum, Bipolaris* spp, *Exserohilum rostratum* and *Histoplasma capsulatum.*

7. The method of claim 1, wherein the defensin and the chemical agent are topically applied to a human or animal.

8. The method of claim 1, wherein the defensin and the chemical agent are non-topically applied to a human or animal.

9. The method of claim 1, wherein the defensin is produced by a genetically modified microorganism or is provided by an extract of a plant or cell.

10. A method for treatment or prophylaxis of a pathogen of a human or animal subject by applying the method of claim 1.

11. A method for inhibiting growth or infestation of a pathogen, the method comprising contacting the pathogen with an effective amount of a combination of a plant defensin selected from the group consisting of TPP3, PhD1, PhD1A, PhD2, FST, NoD173, HXL001, HXL002, HXL004, HXL007, HXL008, HXL009, HXL012, HXL013, HXL015, HXL035 and HXL036 with a β-glucan synthase inhibitor, in a combination of the defensin and the βglucan synthase inhibitor which exhibits a synergistic effect of inhibition of growth of the pathogen, wherein the pathogen is a fungal pathogen selected from the group consisting of *Alternaeria* spp, *Aspergillus* spp, *Candida* spp, *Fusarium* spp, *Trichophyton* spp, *Cryptococcus* spp, *Histoplasma* spp, *Microsporum* spp, *Penicillium* spp, *Pneumocystis* spp *Trichosporon* spp, *Scedosporium* spp, *Paeciliomyces* spp, *Acremonium* spp, *Stachybotrys* spp and Dematiaceous molds.

12. A method for inhibiting growth or infestation of a fungal pathogen, the method comprising contacting the fungal pathogen with an effective amount of a combination of a plant defensin selected from the group consisting of TPP3, PhD1, PhD1A, PhD2, FST, NoD173, HXL001, HXL002, HXL004, HXL007, HXL008, HXL009, HXL012, HXL013, HXL015, HXL035 and HXL036 with a β-glucan synthase inhibitor, in a combination of the defensin and the β-glucan synthase inhibitor which exhibits a synergistic effect of inhibition of growth of the pathogen, wherein the pathogen is a fungal pathogen selected from the group consisting of *Alternaeria* spp, *Aspergillus* spp, *Candida* spp, *Fusarium* spp, *Trichophyton* spp, *Cryptococcus* spp, *Histoplasma* spp, *Microsporum* spp, *Penicillium* spp, *Pneumocystis* spp *Trichosporon* spp, *Scedosporium* spp, *Paeciliomyces* spp, *Acremonium* spp, *Stachybotrys* spp and Dematiaceous molds.

13. The method of claim 11, wherein the β-glucan synthase inhibitor is an echinocandin.

14. The method of claim 13, wherein the echinocandin is caspofungin.

15. The method of claim 12, wherein the β-glucan synthase inhibitor is an echinocandin.

16. The method of claim 15, wherein the echinocandin is caspofungin.

17. The method of claim 1, wherein the pathogen is a fungal pathogen of *Candida* spp.

\* \* \* \* \*